(12) United States Patent
Schiltz et al.

(10) Patent No.: US 12,252,492 B2
(45) Date of Patent: Mar. 18, 2025

(54) SUBSTITUTED FUSED PYRROLO-DIAZEPINONES AND USES THEREOF

(71) Applicant: Northwestern University, Evanston, IL (US)

(72) Inventors: Gary E. Schiltz, Naperville, IL (US); Karl A. Scheidt, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/577,972

(22) Filed: Jan. 18, 2022

(65) Prior Publication Data

US 2022/0135575 A1 May 5, 2022

Related U.S. Application Data

(63) Continuation of application No. 16/295,864, filed on Mar. 7, 2019, now Pat. No. 11,225,483.

(60) Provisional application No. 62/639,770, filed on Mar. 7, 2018.

(51) Int. Cl.
*C07D 487/04* (2006.01)
*A61P 35/00* (2006.01)
*C07D 207/24* (2006.01)

(52) U.S. Cl.
CPC ............ *C07D 487/04* (2013.01); *A61P 35/00* (2018.01); *C07D 207/24* (2013.01)

(58) Field of Classification Search
CPC .................................................. C07D 487/04
See application file for complete search history.

(56) References Cited

U.S. PATENT DOCUMENTS

| | | |
|---|---|---|
| 7,851,640 B2 | 12/2010 | Scheidt |
| 8,481,760 B2 | 7/2013 | Bergan |
| 8,742,141 B2 | 6/2014 | Bergan |
| 8,791,267 B2 | 7/2014 | Singh |

(Continued)

FOREIGN PATENT DOCUMENTS

| | | | |
|---|---|---|---|
| WO | 2008103367 A1 | | 8/2008 |
| WO | WO 2008-103367 | * | 8/2008 |

OTHER PUBLICATIONS

Matsuo et al. (Chem. Pharm. Bull. (1984) 32:(9); p. 3724-3729).*

(Continued)

*Primary Examiner* — Valerie Rodriguez-Garcia
(74) *Attorney, Agent, or Firm* — Quarles & Brady LLP

(57) ABSTRACT

Disclosed are compounds, pharmaceutical compositions, and methods of treatment. The disclosed compounds are based on fused 1,4-diazepine and pyrrolidinedione scaffolds. The compounds may be utilized in pharmaceutical compositions and methods for treating diseases and disorders associated with cell proliferation such as cancer and may have a formula illustrated as follows:

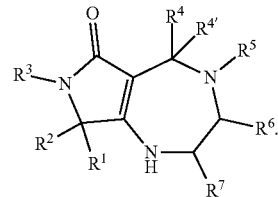

12 Claims, 10 Drawing Sheets

(56) References Cited

U.S. PATENT DOCUMENTS

| | | |
|---|---|---|
| 8,912,341 B2 | 12/2014 | Scheidt |
| 9,090,634 B2 | 7/2015 | Scheidt |
| 9,260,564 B2 | 2/2016 | Lombardo |
| 9,309,217 B2 | 4/2016 | Scheidt |
| 9,334,297 B2 | 5/2016 | Scheidt |
| 9,512,146 B2 | 12/2016 | Scheidt |
| 9,527,812 B2 | 12/2016 | Scheidt |
| 9,624,190 B2 | 4/2017 | Scheidt |
| 9,643,947 B2 | 5/2017 | Scheidt |
| 9,669,014 B2 | 6/2017 | Siddique |
| 9,688,637 B2 | 6/2017 | Schiltz |
| 9,839,625 B2 | 12/2017 | Bergan |
| 9,840,487 B2 | 12/2017 | Scheidt |
| 9,981,968 B2 | 5/2018 | Schiltz |
| 10,093,668 B2 | 10/2018 | Schiltz |
| 10,231,949 B2 | 3/2019 | Bergan |
| 10,308,624 B2 | 6/2019 | Scheidt |
| 10,323,039 B2 | 6/2019 | Scheidt |
| 10,435,375 B2 | 10/2019 | Schiltz |
| 2006/0258637 A1 | 11/2006 | Hirama |
| 2009/0124569 A1 | 5/2009 | Bergan |
| 2012/0283313 A1 | 11/2012 | Bergan |
| 2017/0253581 A1 | 9/2017 | Schiltz |
| 2018/0244654 A1 | 8/2018 | Schiltz |
| 2019/0062281 A1 | 2/2019 | Schiltz |
| 2019/0201373 A1 | 7/2019 | Bergan |
| 2019/0300540 A1 | 10/2019 | Scheidt |

OTHER PUBLICATIONS

Arkin, M. R. et al., Small-molecule inhibitors of protein-protein interactions: progressing towards the dream. Nat Rev Drug Discov 2004, 3 (4), 301-17.

Boyd, M. R. et al., Some practical considerations and applications of the national cancer institute in vitro anticancer drug discovery screen. Drug Development Research 1995, 34 (2), 91-109.

Cui, J. et al., Synthesis of a high-purity chemical library reveals a potent inducer of oxidative stress. ChemBioChem 2010, 11 (9), 1224-7.

Di Braccio, M. et al., 1,5-Benzodiazepines. Part XII. Synthesis and biological evaluation of tricyclic and tetracyclic 1,5-benzodiazepine derivatives as nevirapine analogues. Eur. J. Med. Chem. 2001, 36 (11-12), 935-949.

Filippakopoulos, P. et al., Selective inhibition of BET bromodomains. Nature 2010, 468 (7327), 1067-73.

Holloway, C. A. et al., Novel chiral skeletons for drug discovery: antibacterial tetramic acids. Chemical biology & drug design 2011, 78 (2), 229-35.

Horton, D. A. et al., The Combinatorial Synthesis of Bicyclic Privileged Structures or Privileged Substructures. Chem. Rev. 2003, 103 (3), 893-930.

International Searching Authority, International Search Report and Written Opinion for application PCT/US2019/021185, mailed on Jun. 20, 2019.

Jeong, Y.-C. et al., Tetramic Acids as Scaffolds: Synthesis, Tautomeric and Antibacterial Behaviour. Synlett 2009, 2009 (15), 2487-2491.

Lipinski, C. A. et al., Experimental and computational approaches to estimate solubility and permeability in drug discovery and development settings. Adv. Drug Deliv. Rev. 1997, 23 (1-3), 3-25.

Lipinski, C. et al., Navigating chemical space for biology and medicine. Nature 2004, 432 (7019), 855-61.

Lovering, F. et al., Escape from flatland: increasing saturation as an approach to improving clinical success. J Med Chem 2009, 52 (21), 6752-6.

Matsuo, K. et al. "Syntheses of the Novel Furo [3, 4-b][1, 5] benzodiazepinone and Pyrrolo [3, 4-b][1, 5] benzodiazepinone Systems." Chemical and pharmaceutical bulletin 32.9 (1984): 3724-3729.

Matsuo, K., et al. "Synthesis and Reaction of Dihydrofuro [3, 4-b][1, 5] benzodiazepinones and Dihydropyrrolo [3, 4-b][1, 5] benzodiazepinones." Yakugaku zasshi: Journal of the Pharmaceutical Society of Japan 106.8 (1986): 715.

Merluzzi, V. J. et al., Inhibition of HIV-1 replication by a non-nucleoside reverse transcriptase inhibitor. Science 1990, 250 (4986), 1411-1413.

National Cancer Institutes. dtp.cancer.gov/discovery_development/nci-60/methodology.htm. Last updated on Aug. 26, 2015.

Nicodeme, E. et al., Suppression of inflammation by a synthetic histone mimic. Nature 2010, 468 (7327), 1119-23.

Rosenstrom, U. et al., Design, synthesis, and incorporation of a beta-turn mimetic in angiotensin II forming novel pseudopeptides with affinity for AT1 and AT2 receptors. J Med Chem 2006, 49 (20), 6133-7.

Royles, B. J. L., Naturally Occurring Tetramic Acids: Structure, Isolation, and Synthesis. Chem. Rev. 1995, 95 (6), 1981-2001.

Rzuczek, S. G. et al., Precise small-molecule recognition of a toxic CUG RNA repeat expansion. Nat Chem Biol 2017, 13 (2), 188-193.

Shoemaker, R. H., The NCI60 human tumour cell line anticancer drug screen. Nat. Rev. Cancer 2006, 6 (10), 813-23.

Skehan, P. et al., New colorimetric cytotoxicity assay for anticancer-drug screening. J Natl Cancer Inst 1990, 82 (13), 1107-12.

Souers, A. J. et al., ABT-199, a potent and selective BCL-2 inhibitor, achieves antitumor activity while sparing platelets. Nat. Med. 2013, 19 (2), 202-8.

Velagapudi, S. P. et al., Design of a small molecule against an oncogenic noncoding RNA. Proc Natl Acad Sci U S A 2016, 113 (21), 5898-903.

Welsch, M. E. et al., Privileged scaffolds for library design and drug discovery. Curr Opin Chem Biol 2010, 14 (3), 347-61.

\* cited by examiner

| Compound (NUCC) | Percent Viability (50 uM) against MDA-MB-468 cells |
|---|---|
| 202507 | 36.1 |
| 202516 | 50.0 |
| 202773 | 70.4 |
| 202774 | 56.1 |
| 202775 | 79.5 |
| 202776 | 71.0 |
| 202777 | 74.5 |
| 202778 | 57.7 |
| 202779 | 88.5 |
| 202780 | 45.7 |
| 202781 | 79.7 |
| 202782 | 25.3 |
| 202783 | 52.9 |
| 202784 | 50.3 |
| 202785 | 65.2 |
| 202786 | 56.7 |
| 202787 | 60.7 |
| 202788 | 42.7 |
| 202789 | 87.4 |
| 202790 | 45.8 |
| 202791 | 81.6 |

Figure 7

SUBSTITUTED FUSED PYRROLO-DIAZEPINONES AND USES THEREOF

CROSS-REFERENCE TO RELATED PATENT APPLICATIONS

The present application is a continuation of U.S. application Ser. No. 16/295,864, filed Mar. 7, 2019, which claims the benefit of priority under 35 U.S.C. § 119(e) to U.S. Provisional Application No. 62/639,770, filed Mar. 7, 2018, the contents of each of which are incorporated herein by reference in their entirety.

BACKGROUND

The field of the invention relates to fused pyrrolo-diazepinones. In particular, the field of the invention relates to substituted fused pyrrolo-diazepinones and uses thereof for treating diseases and disorders such as cell proliferative diseases and disorders such as cancers.

Over 200,000 people a year in the U.S. are diagnosed with lung cancer each year. It is by far the leading cause of cancer death among both men and women. The lung cancer five-year survival rate (17.7 percent) is lower than many other leading cancer sites, such as the colon (64.4 percent), breast (89.7 percent) and prostate (98.9 percent). The five-year survival rate for lung cancer is 55 percent for cases detected when the disease is still localized (within the lungs). However, only 16 percent of lung cancer cases are diagnosed at an early stage. For distant tumors (spread to other organs) the five-year survival rate is only 4 percent. More than half of people with lung cancer die within one year of being diagnosed.

Existing small molecule agents for lung cancer are typically alkylating agents of microtubule stabilizing agents, each of which produces major side effects. Development of new drugs for lung cancer and other cancers and persistent diseases will increasingly rely on the expansion of accessible chemical space to allow exploration of novel molecular targets. Here we report the synthesis of a library of novel fused heterobicyclic small molecules based on 1,4-diazepine and 2,4-pyrrolidinedione scaffolds. Key chemical transformations included a Mannich-type condensation and a chemoselective N-acylation reactions. Screening of these new compounds demonstrates that the new compounds have anti-cancer activity which suggests translational potential of this novel chemical scaffold. Some compounds have particular efficacy against lung cancer cells in vitro.

SUMMARY

Disclosed are compounds, pharmaceutical compositions, and methods of treatment. The disclosed compounds are based on fused 1,4-diazepine and pyrrolidinedione scaffolds and may described as compounds having the following core and substituted derivatives thereof:

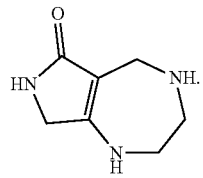

The compounds may be utilized in pharmaceutical compositions and methods for treating diseases and disorders associated with cell proliferation. In particular, the compounds may be utilized in pharmaceutical compositions and methods for treating cancer.

The disclosed compounds may be formulated as pharmaceutical compositions comprising one or more of the disclosed compounds, a tautomer thereof, or a pharmaceutical salt thereof, and a suitable pharmaceutical carrier. The disclosed compounds or pharmaceutical compositions comprising the disclosed compounds may be administered to a subject in need thereof, for example, to treat a disease or disorder associated with cell proliferation such as cancer.

BRIEF DESCRIPTION OF THE FIGURES

FIG. 7. Percent viability of compounds (50 µM) against MDA-MB-468 breast cancer cells after treatment with the listed compounds.

DETAILED DESCRIPTION

Figure 1:
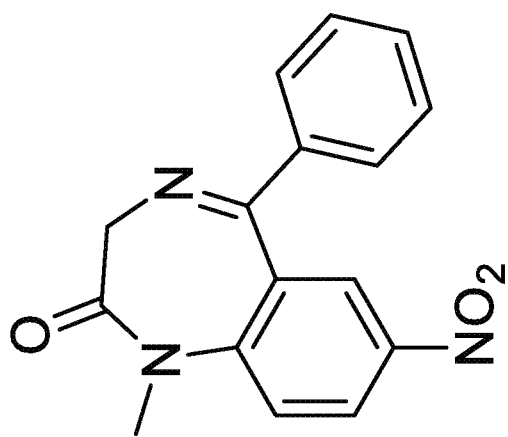
FIG. 1. Examples of pharmacologically relevant diazepine-containing compounds.
Figure 1:
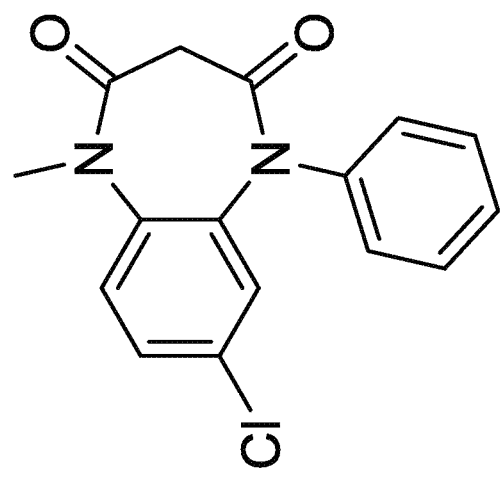
Figure 1:
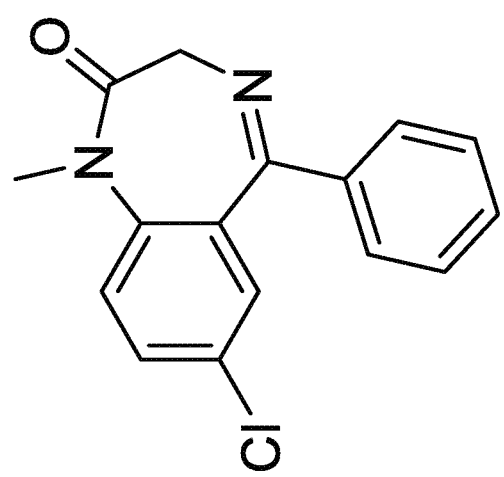
Figure 2:
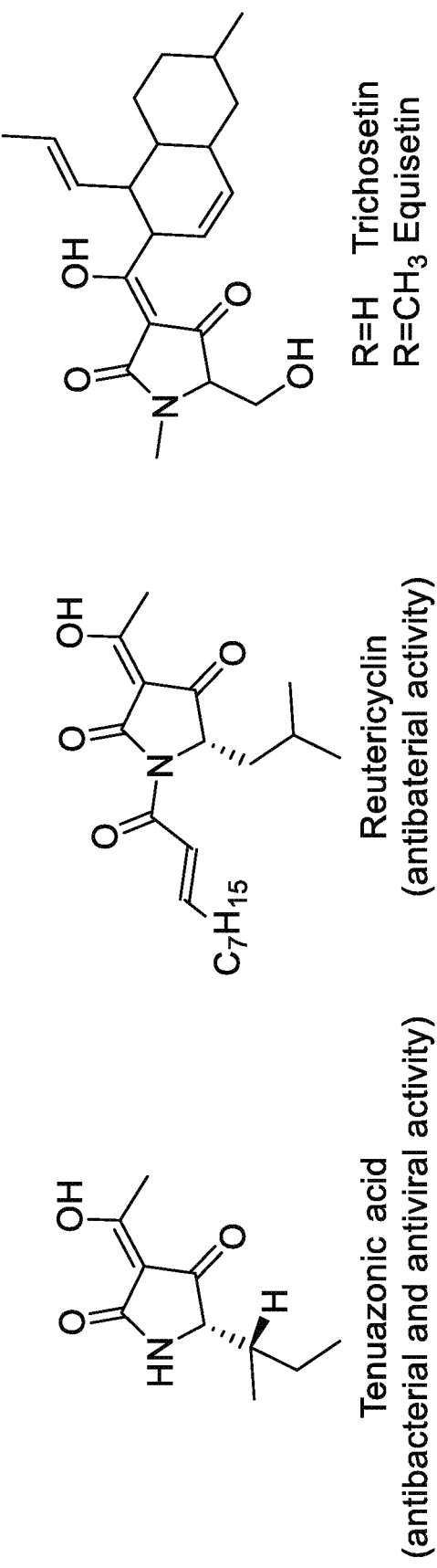
FIG. 2. Representative natural products containing the tetramic acid scaffold.
Figure 3:
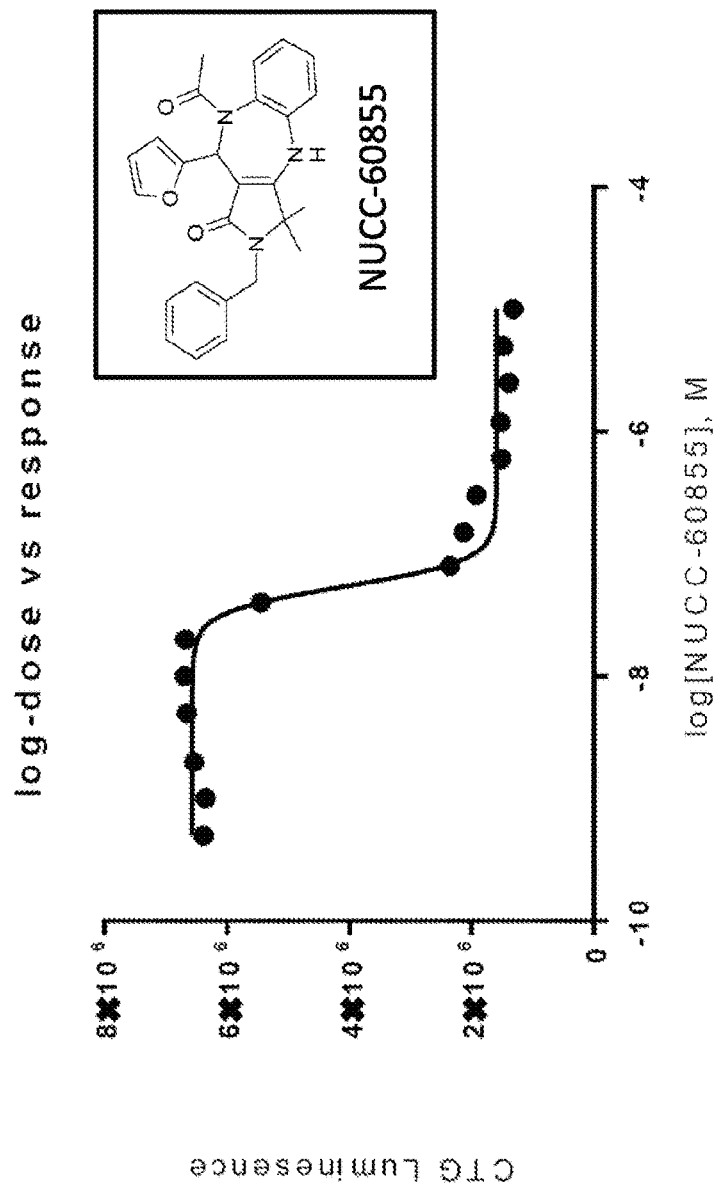
FIG. 3. A459 cell viability after 3-day treatment with compound NUCC-60855 at the indicated concentrations.
Figure 4:
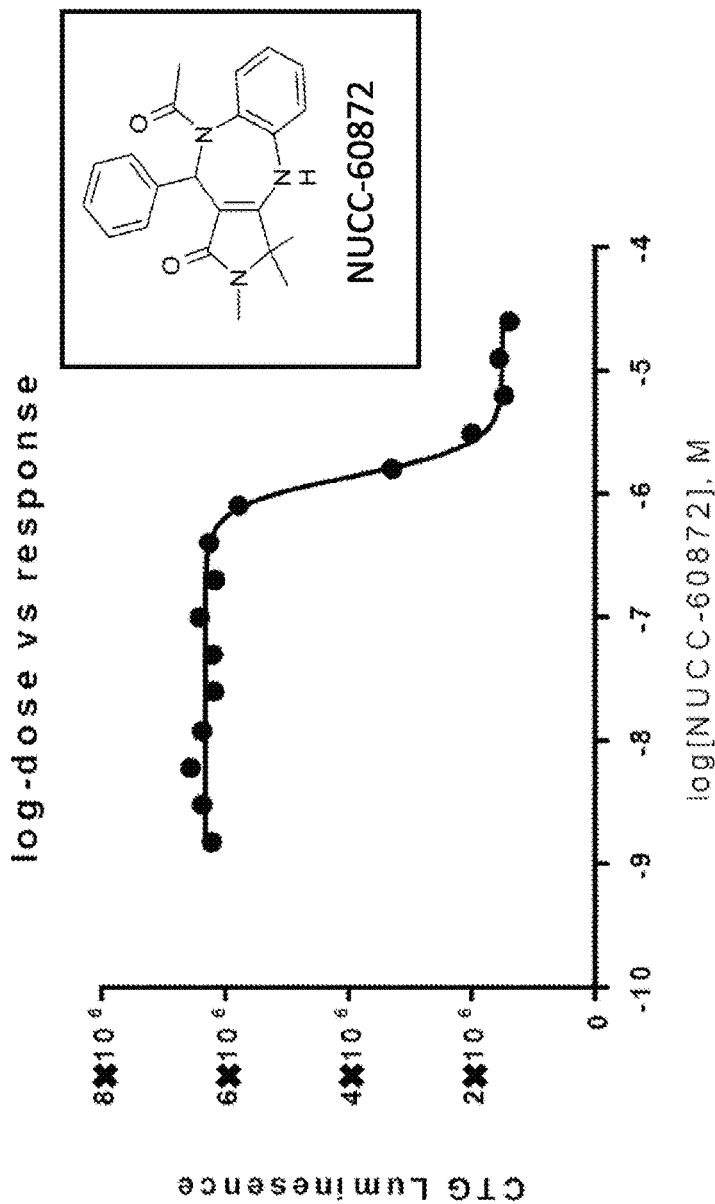
FIG. 4. A459 cell viability after 3-day treatment with compound NUCC-60872 at the indicated concentrations.
Figure 5:
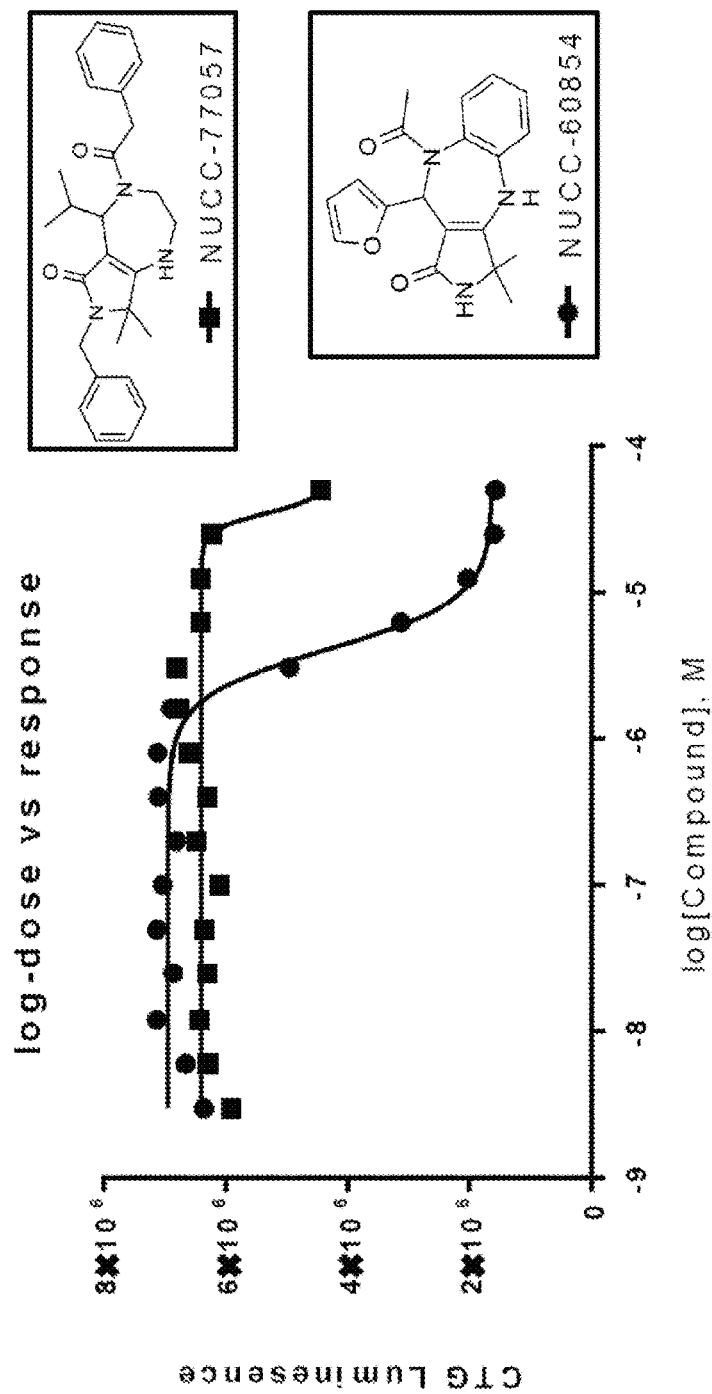
FIG. 5. A459 cell viability after 3-day treatment with compound NUCC-60854 or NU-77057 at the indicated concentrations.
Figure 6:
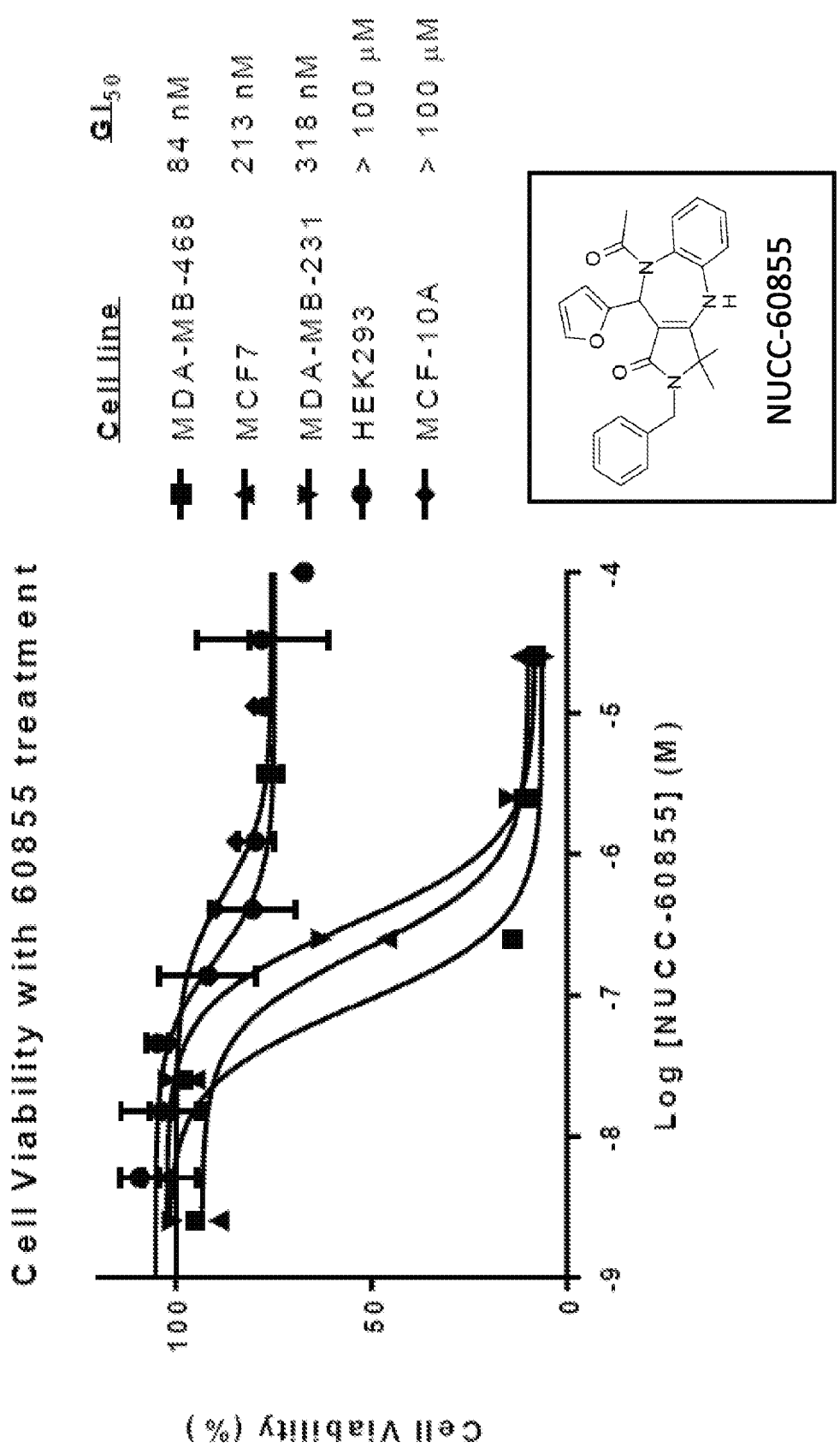
FIG. 6. Cell viability data for compound NUCC-60855 against breast cancer cells and normal cells. Cells were treated for two (2) days.
Figure 8:
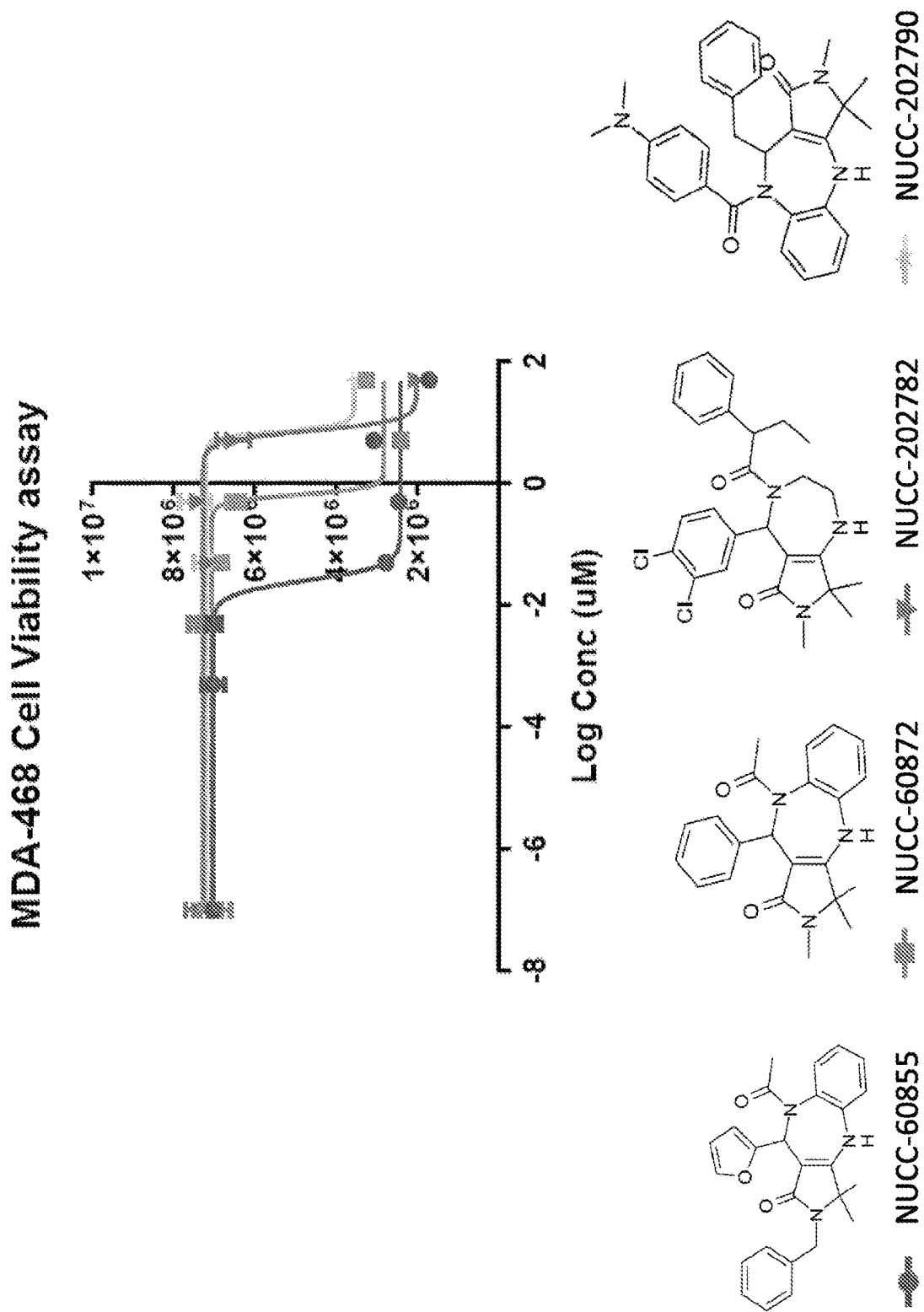
FIG. 8. MDA-468 cell viability assay in the presence of compounds NUCC-60855, NUCC-60872, NUCC-202782, and NUCC-202790.
Figure 9:
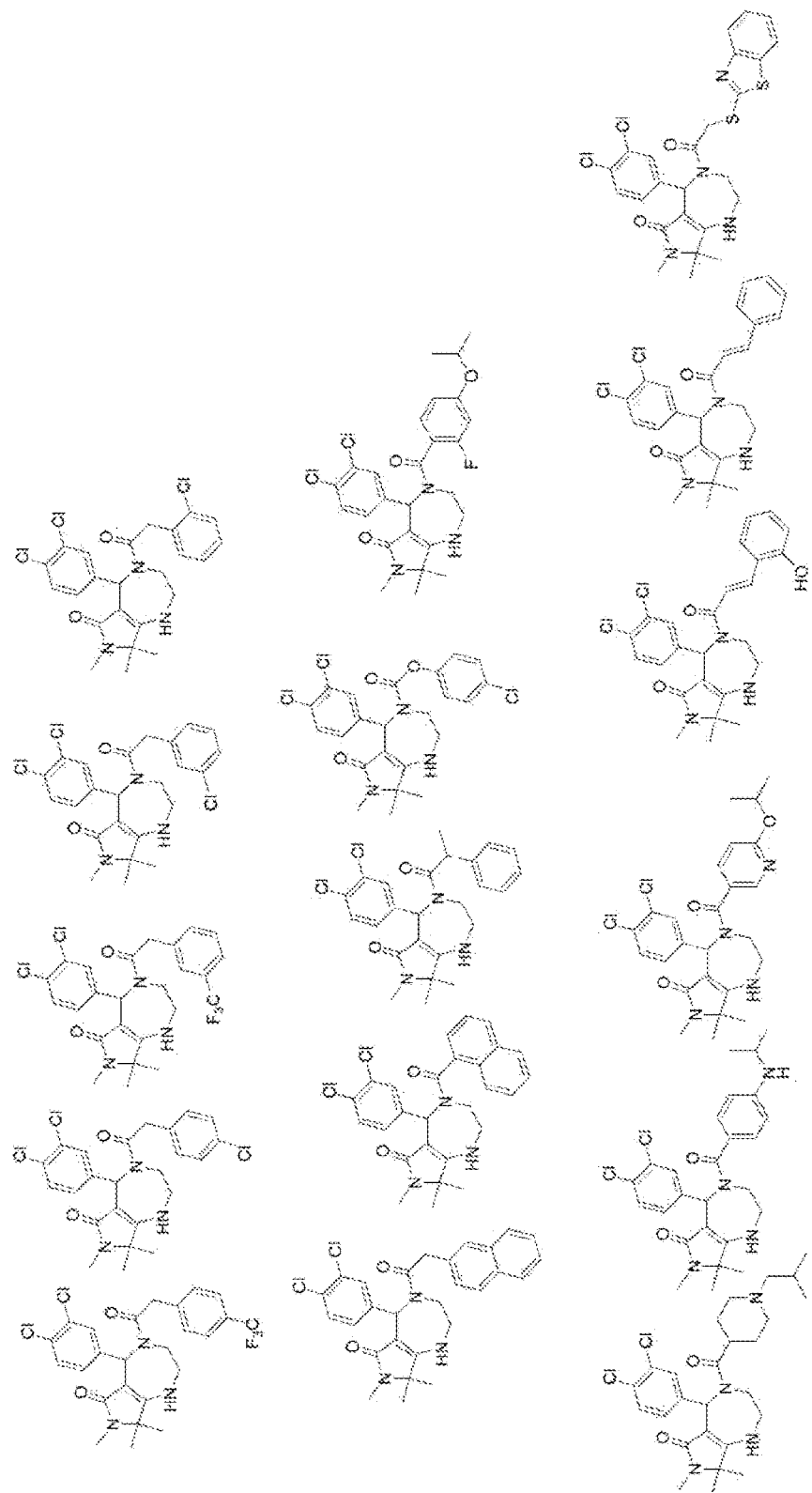
FIG. 9. Additional derivative compound that can be synthesized by the methods disclosed herein.
Figure 10:
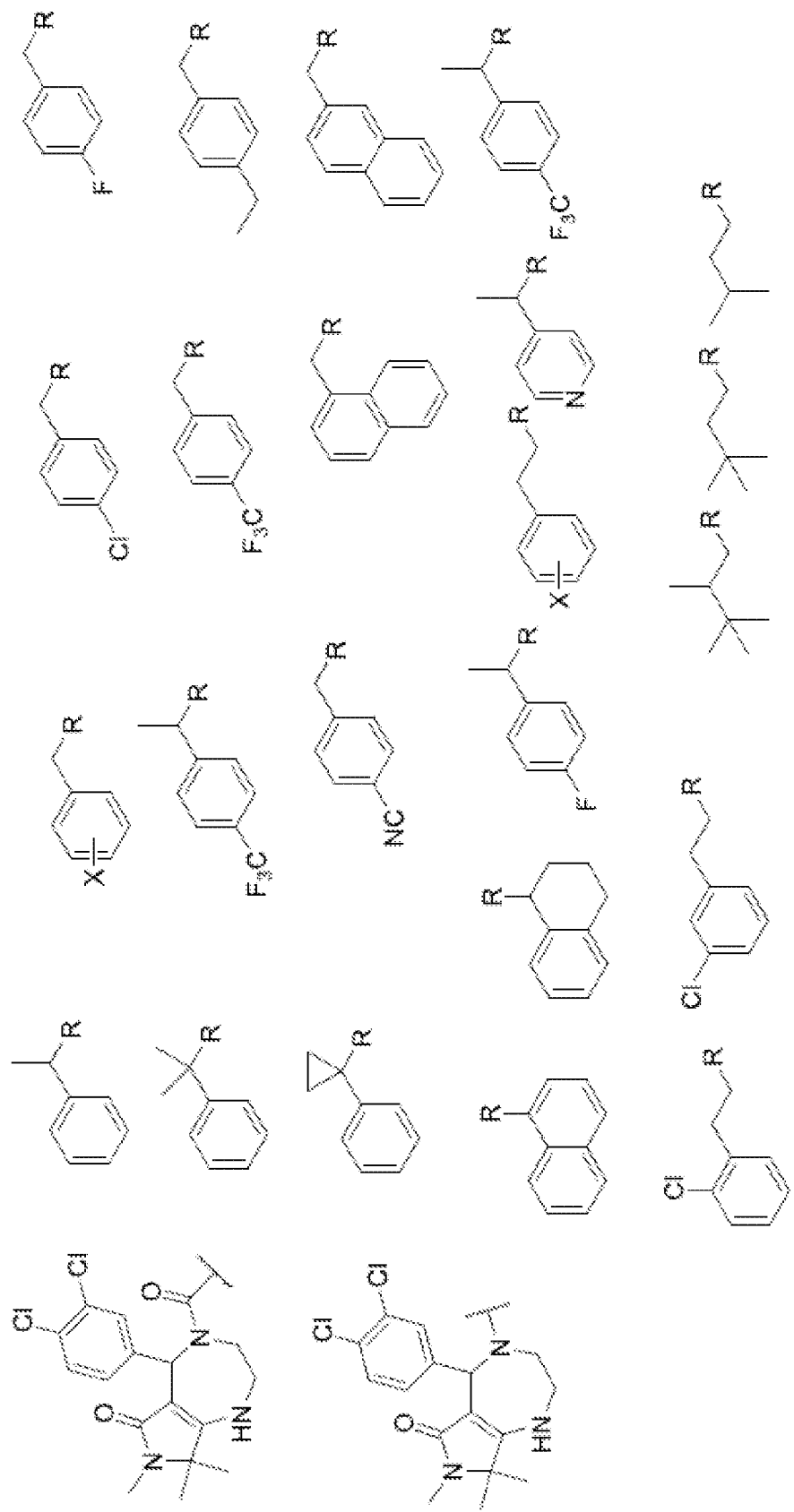
FIG. 10. Additional derivative compound that can be synthesized by the methods disclosed herein where "R" indicates the point of attachment of the substituent to the fused core structure at the oxo group (top structure) or at the diazepine nitrogen atom (bottom structure).

As used herein, unless otherwise specified or indicated by context, the terms "a", "an", and "the" mean "one or more." For example, "a compound" or "a substituent" should be interpreted to mean "one or more compounds" and "one or more substituents," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment, for example, treatment by include administering a therapeutic amount of one or more compounds or pharmaceutical compositions as disclosed herein.

A "subject in need of treatment" may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as $C_1$-$C_{12}$ alkyl, $C_1$-$C_{10}$-alkyl, and $C_1$-$C_6$-alkyl, respectively.

The term "alkylene" refers to a diradical of an alkyl group (e.g., —$(CH_2)_n$— where n is an integer such as an integer between 1 and 20). An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$-alkynyl, $C_2$-$C_{10}$-alkynyl, and $C_2$-$C_6$-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen.

Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R, for example, may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R'C(O)N(R²)—, —R'C(O)N(R²)R³—, —C(O)NR²R³, or —C(O)NH₂, wherein R', R² and R³, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The term "amino protecting group" is known in the art and may include, but is not limited to t-butyl carbamate (BOC), p-methoxybenzyl (PMB), 9-fluorenylmethyl carbamate (FMOC), benzyl carbamate (Cbz), acetamide (Ac), trifluoroacetamide, phthalimide, benzylamine (Bn), triphenylmethylamine (Tr), benzylideneamine, and p-toluenesulfonamide (Ts).

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound). The compounds may have an undefined double stereo bond whose substituents may be present in either of the syn-conformation or the anti-conformation (or alternatively in the E-conformation or the Z-conformation).

Substituted Fused Pyrrolo-Diazepinones and Uses Thereof

Disclosed are compounds, pharmaceutical compositions, and method of treatment. The disclosed compounds are based on fused 1,4-diazepine and pyrrolidinedione scaffolds and may described as compounds having the following core or substituted derivatives thereof:

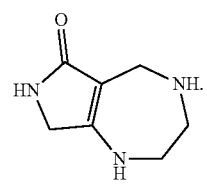

The compounds may be utilized in pharmaceutical compositions and methods for treating diseases and disorders associated with cell proliferation. In particular, the compounds may be utilized in pharmaceutical compositions and methods for treating cancer.

The disclosed compounds may be formulated as pharmaceutical compositions comprising one or more of the disclosed compounds, a tautomer thereof, or a pharmaceutical salt thereof, and a suitable pharmaceutical carrier. The disclosed compounds or pharmaceutical compositions comprising the disclosed compounds may be administered to a subject in need thereof, for example, to treat a disease or disorder associated with cell proliferation such as cancer.

The compounds disclosed herein may exist in one or more tautomeric forms as known in the art. The disclosed compounds therefore encompass tautomeric derivatives as would be known in the art. The compounds disclosed herein may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.) As used herein, formulae which do not specify the orientation at one or more chiral centers are meant to encompass all orientations and mixtures thereof.

Pharmaceutical Compositions

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that treats cancer may be administered as a single compound or in combination with another compound that treats cancer or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds disclosed herein or salts, esters, and/or amides, thereof. Solvate forms may include ethanol solvates, hydrates, and the like.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |

-continued

| | Quantity (mg/tablet) |
|---|---|
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

| | Weight % |
|---|---|
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| Active Ingredient | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose can be prepared as follows:

| Active Ingredient | 100 mg |
|---|---|
| Mannitol | 100 mg |
| 5N Sodium hydroxide | 200 ml |
| Purified water to total | 5 n |

ILLUSTRATIVE EMBODIMENTS

The following embodiments are illustrative and should not be interpreted to limit the scope of the claimed subject matter.

Embodiment 1

A compound or a salt thereof having a formula:

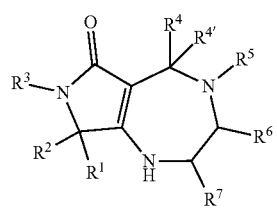

wherein:

$R^1$ and $R^2$ are H or alkyl;

$R^3$ is H, alkyl, alkenyl (e.g. isopentenyl), or benzyl;

R⁴ is H, alkyl (e.g., methyl or isobutyl), benzyl, or a carbocycle (e.g., a 3-, 4-, 5-, or 6-membered carbocycle such as cycloalkyl or phenyl), a heterocycle (e.g., a 3-, 4-, 5-, or 6-membered heterocycle such as piperidinyl, pyridinyl, or thiophenyl), two fused carbocycles (e.g., two fused 3-, 4-, 5-, or 6-membered carbocycles such as naphthalene), two fused heterocycles (e.g., two fused 3-, 4-, 5-, or 6-membered heterocycles such as purine), or a fused carbocycle and a fused heterocycle (e.g., a fused 3-, 4-, 5-, or 6-membered carbocycle and a fused 3-, 4-, 5-, or 6-membered heterocycle such as 1,3-benzodioxolyl or 1,4-benzodioxanyl), which carbocycle and heterocycle are saturated or unsaturated at one or more bonds and optionally are substituted at one or more positions with halo (e.g., 3,4-dichlorophenyl), alkyl, haloalkyl, methoxy (e.g. 4-methoxyphenyl), or carboxyl (e.g., 4-carboxyphenyl), or carboxy;

R⁴' is H or alkyl;

R⁵ is H, alkyl, aryl such as phenyl, alkylaryl such as benzyl, sulfonyl, and R⁵ optionally is substituted at one or more positions with alkyl, halo, haloalkyl, alkoxy, cyano, amino or alkyl-substituted amino, or R⁵ has a formula

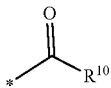

where $R^{10}$ is H, alkyl, phenylamino, benzyl, or $R^{10}$ is a carbocycle (e.g., a 3-, 4-, 5-, or 6-membered carbocycle such as cycloalkyl or phenyl), a heterocycle (e.g., a 3-, 4-, 5-, or 6-membered heterocycle such as piperidinyl, pyridinyl, or thiophenyl), two fused carbocycles (e.g., two fused 3-, 4-, 5-, or 6-membered carbocycles such as naphthalene), two fused heterocycles (e.g., two fused 3-, 4-, 5-, or 6-membered heterocycles such as purine), or a fused carbocycle and a fused heterocycle (e.g., a fused 3-, 4-, 5-, or 6-membered carbocycle and a fused 3-, 4-, 5-, or 6-membered heterocycle such as 1,3-benzodioxolyl or 1,4-benzodioxanyl), which carbocycle and heterocycle are saturated or unsaturated at one or more bonds and $R^{10}$ optionally is substituted at one or more positions with halo, alkyl, alkoxy (e.g., where $R^{10}$ is 4-methoxyphenyl), amino or substituted amino which optionally is alkylamino or dialkylamino (e.g., where $R^{10}$ is 4-(N,N-dimethylamino)phenyl), haloalkyl (e.g., where $R^{10}$ is 4-trifluormethylphenyl) or carboxy; or $R^{10}$ has a formula

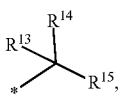

wherein $R^{13}$ is H or alkyl, $R^{14}$ is H or alkyl or $R^{13}$ and $R^{14}$ together form cycloalkyl, a $R^{15}$ is benzyl or oxybenzyl, or a carbocycle (e.g., a 3-, 4-, 5-, or 6-membered carbocycle such as cycloalkyl or phenyl), a heterocycle (e.g., a 3-, 4-, 5-, or 6-membered heterocycle such as piperidinyl, pyridinyl, or thiophenyl), two fused carbocycles (e.g., two fused 3-, 4-, 5-, or 6-membered carbocycles such as naphthalene), two fused heterocycles (e.g., two fused 3-, 4-, 5-, or 6-membered heterocycles such as purine), or a fused carbocycle and a fused heterocycle (e.g., a fused 3-, 4-, 5-, or 6-membered carbocycle and a fused 3-, 4-, 5-, or 6-membered heterocycle such as 1,3-benzodioxolyl or 1,4-benzodioxanyl), which carbocycle and heterocycle are saturated or unsaturated at one or more bonds and $R^{15}$ optionally is substituted at one or more positions with halo, alkyl, haloalkyl, alkoxy, amino or substituted amino which optionally is alkylamino or dialkylamino, or carboxy; and $R^6$ and $R^7$ are H, or $R^6$ and $R^7$ together form phenyl fused to the 1.4-diazepine core.

Embodiment 2

The compound of embodiment 1, wherein $R^1$ and $R^2$ are methyl.

Embodiment 3

The compound of embodiment 1 or 2, wherein $R^3$ is methyl.

Embodiment 4

The compound of any of the foregoing embodiments, wherein $R^4$ is selected from methyl, isopropyl, cyclopropyl, cyclobutyl, cyclopentyl, cyclohexyl, furanyl (e.g., furan-2-yl), pyridinyl (e.g., pyridin-2-yl, pyridin-3-yl or pyridin-4-yl), phenyl or fluorophenyl (e.g., 4-flurophenyl) or chlorophenyl (e.g., 4-chlorophenyl or 3,4-dichlorophenyl) or carboxyphenyl (e.g., 4-carboxyphenyl) or methoxyphenyl (e.g., 4-methoxyphenyl), benzyl, thiophenyl (e.g., thiophen-2-yl or thiophen-3-yl) or chlorothiophenyl (e.g., 5-chlorothiophen-2-yl), tetrahydrofuranyl (e.g., tetrahydrofuran-2-yl or tetrahydrofuran-3-yl), thiazolyl (e.g., thiazol-2-yl), 1,3-benzodioxolyl (e.g., 1,3-benzodioxol-5-yl), 1,4-benzodioxanyl (e.g., 1,4-benzodioxan-6-yl), and piperidinyl (e.g., 4-piperidinyl).

Embodiment 5

The compound of any of the foregoing embodiments, wherein $R^5$ has a formula

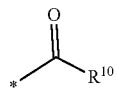

and $R^{10}$ is methyl, tetrabutyl, isopropyl, cyclopropyl, cyclobutyl, cyclopentyl, cyclohexyl, thiophenyl (e.g., thiophen-2-yl), 4-(N,N-diakylamino)phenyl, 4-trifluoromethylphenyl, 4-methoxyphenyl, 4-fluorophenyl, phenylamino, 1,3-benzodioxolyl (e.g., 1,3-benzodioxol-5-yl), 1,4-benzodioxanyl (e.g., 1,4-benzodioxan-6-yl), pyridinyl (e.g., pyridin-2-yl, pyridin-3-yl, pyridin-4-yl), amino or alkylamino (e.g., dialkylamino), phenyl, tetrahydropyranyl, (e.g., tetrahydropyran-4-yl).

Embodiment 6

The compound of any of the foregoing embodiments, wherein $R^5$ has a formula

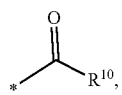

$R^{10}$ has a formula

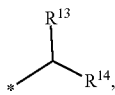

$R^{13}$ is H, and $R^{14}$ is phenyl, oxybenzyl, tetrahydropyranyl, (e.g., tetrahydropyran-4-yl), or 1,3-benzodioxolyl (e.g., 1,3-benzodioxol-5-yl).

Embodiment 7

The compound of any of the foregoing embodiments, wherein $R^4$ is benzyl and $R^5$ is oxobenzyl.

Embodiment 8

A pharmaceutical composition comprising any effective amount of the compound of any of the foregoing embodiments and a pharmaceutical carrier, excipient, or diluent.

Embodiment 9

A method for treating a disease or disorder in a subject in need thereof, the method comprising administering to the subject the pharmaceutical composition of embodiment 8.

Embodiment 10

The method of embodiment 9, wherein the disease or disorder is a cell proliferative disease or disorder.

Embodiment 11

The method of embodiment 9, wherein the disease or disorder is cancer, optionally wherein the cancer is selected from adenocarcinoma, leukemia, lymphoma, melanoma, myeloma, sarcoma, and teratocarcinoma and/or the cancer is selected from cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

Embodiment 12

A compound of Table 2 in the Specification that accompanies these embodiments.

Embodiment 13

A pharmaceutical composition comprising any effective amount of the compound of embodiment 12 and a pharmaceutical carrier, excipient, or diluent.

Embodiment 14

A method for treating a disease or disorder in a subject in need thereof, the method comprising administering to the subject the pharmaceutical composition of embodiment 13.

Embodiment 15

The method of embodiment 14, wherein the disease or disorder is a cell proliferative disease or disorder, optionally wherein the disease or disorder is cancer, optionally wherein the cancer is selected from adenocarcinoma, leukemia, lymphoma, melanoma, myeloma, sarcoma, and teratocarcinoma and/or the cancer is selected from cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

Embodiment 16

A compound having a structure:

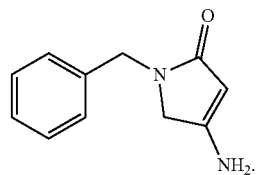 [SMILES: NC1=CC(=O)N(Cc2ccccc2)C1]

Embodiment 17

A compound having a structure:

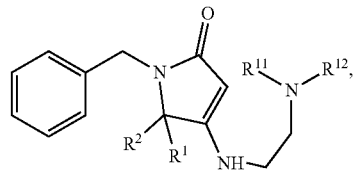

wherein $R^1$ and $R^2$ are H or alkyl and $R^{11}$ and $R^{12}$ are H or an amino protecting group (e.g., t-butyl carbamate (BOC), p-methoxybenzyl (PMB), 9-fluorenylmethyl carbamate (FMOC), benzyl carbamate (Cbz), acetamide (Ac), trifluoroacetamide, phthalimide, benzylamine (Bn), triphenylmethylamine (Tr), benzylideneamine, and p-toluenesulfonamide (Ts)).

Embodiment 18

The compound of embodiment 17, wherein $R^1$ and $R^2$ are methyl and $R^{11}$ and $R^{12}$ are H.

Embodiment 19

A compound having a structure:

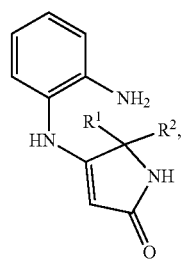

wherein $R^1$ and $R^2$ are H or alkyl.

Embodiment 20

The compound of embodiment 19, wherein $R^1$ and $R^2$ are methyl.

Examples

The following Examples are illustrative and are not intended to limit the scope of the claimed subject matter.

Synthesis of a Novel Fused Pyrrolodiazepine-Based Library with Anti-Cancer Activity Reference is made to the manuscript entitled Malik et al., "Synthesis of a Novel Fused Pyrrolodiazepine-Based Library with Anti-Cancer Activity," Tetrahedron Letters, Volume 59, Issue 15, 11 Apr. 2018, Pages 1513-1516, the content of which is incorporated herein by reference in its entirety.

Abstract

Development of drugs for new and persistent diseases will increasingly rely on the expansion of accessible chemical space to allow exploration of novel molecular targets. Here we report the synthesis of a library of novel fused heterobicyclic small molecules based on the 1,4-diazepine and 2,4-pyrrolidinedione scaffolds. Key chemical transformations included a Mannich-type condensation and chemoselective N-acylation reactions. Screening shows anti-cancer activity of several library compounds which suggests translational potential of this novel chemical scaffold.

Graphical Scheme

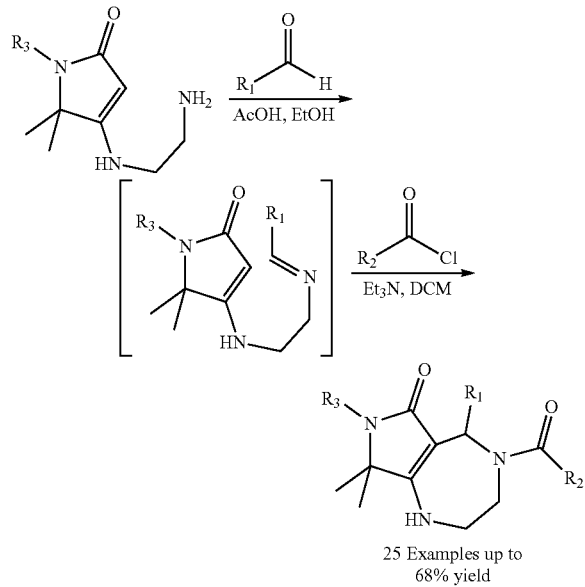

25 Examples up to 68% yield

INTRODUCTION

There is a continuous need for the generation of small molecule libraries to identify new lead compounds for drug discovery against novel targets: Incorporation of key scaffolds or pharmacophore-based structural features during the design of such small molecules aids in studying diverse biological targets. For instance, molecular frameworks containing the diazepine scaffold have been recognized to have significant medicinal relevance.[2] The benzodiazepines motif, for example, is considered a 'privileged structures' with derivatives having a broad range of biological activity such as against central nervous system disorders,[3] anti-HIV,[4-5] anti-malarial and anti-cancer[6-7] therapeutics. The benzodiazepine system is thought to have such wide utility in part because of its ability to mimic peptide β- and γ-turn moieties.[8]

Synthetic agents and natural products containing the 2,4-pyrrolidinedione ring system or tetramic acid core have similarly been shown to have promising biological activity for a number of important indications.[9-11]

Synthesis of tricyclic chemical compounds containing the 1,4-benzodiazepine and tetramic acid subunits has previously been documented.[12] Such tricyclic pyrrolobenzodiazepine derivatives have been synthesized by the condensation reaction of enaminolactams with the corresponding aldehydes.[12-13] While some of these compounds produced interesting biological activity,[12] the addition of the third ring onto the benzodiazepine core would be expected to produce effects divergent from those of classical bicyclic fused benzodiazepines which mimic β-turn peptide features.[8]

To the best of our knowledge there have been no reports on the synthesis of bicyclic systems resulting from the fusion of 1,4-diazepine and 2,4-pyrrolidinedione subunits. This is interesting to note since the bicyclic ring system would be expected to possess lower CLogP values than the tricylic system,[14] making them potentially more suitable as therapeutics.

Herein, we describe the synthesis of a novel series of bicyclic pyrrolodiazepines comprised of the 1,4-diazepine and 2,4-pyrrolidinedione subunits. This work enables the synthesis of a wide variety of diverse and novel drug-like compounds for potential biomedical applications. They may therefore be of great interest to medicinal chemists looking to prepare molecules that access new chemical space for novel drug targets.

Results

The overall synthetic approach is based on previously reported synthesis of furobenzodiazepines and pyrrolobenzodiazepines by Matsuo and Tanaka.[13] Vinylogous urea 6 was synthesized in six steps from commercially available amino acid ester 1 as illustrated in Scheme 1. Reductive amination of amino acid ester 1 with benzaldehyde using NaBH$_4$ as the reducing agent gave the corresponding secondary amine 2 in excellent yield (98%). N-acylation of amine 2 with ethyl 3-chloro-3-oxopropanoate in the presence of triethylamine (TEA) as base gave the intermediate diester. Interestingly, the intermediate acyclic amide could not be isolated as TEA was sufficient to promote the immediate Dieckmann condensation to form 5-membered ring 3 in 60% yield. Hydrolysis-decarboxylation of keto-ester 3 using aqueous AcOH provided pyrrolidinedione 4 in excellent yield (82%). Boc-protected enaminolactam 5 was obtained in 82% yield by treating 4 with tert-butyl (2-aminoethyl)carbamate in the presence of a catalytic amount of pTsOH. Finally, removal of the boc-protecting group afforded the desired vinylogous urea 6 in excellent yield (92%) which could enable further wide structural diversification. This rapid and efficient six step synthetic route furnished vinylogous urea 6 in an overall 36% yield.

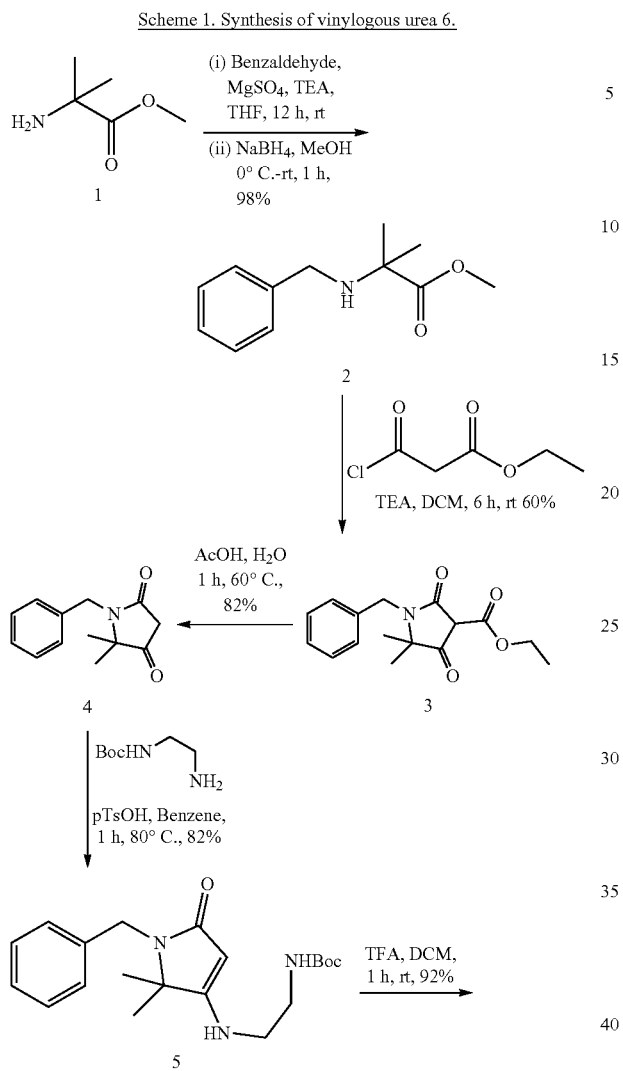

were used to provide the final compounds 8a-8y. The sulfonamide could also be formed by using methanesulfonyl chloride and TEA (8j).

With the key vinylogous urea 6 in hand, we were able to synthesize the final pyrrolodiazepine-based compound library by diversification at two key sites. Scheme 2 depicts the sequence for generation of the desired library of compounds Mannich-type condensation of 6 with various aldehydes ($R_1$CHO) in the presence of AcOH proceeded smoothly to give the corresponding bicyclic amines 7. These reaction conditions were found to be compatible with various aldehydes including heteroaromatic and aliphatic aldehydes Amines 7a-c were found to degrade when purification was attempted using normal phase flash chromatography and were therefore used without further purification. The crude amines (7a-c) were immediately subjected to chemoselective N-acylation reactions. Diverse acid chlorides ($R_2$COCl) including aliphatic, heterocyclic, and aromatic TABLE 1-continued
Synthesis of bicyclic pyrrolodiazepines
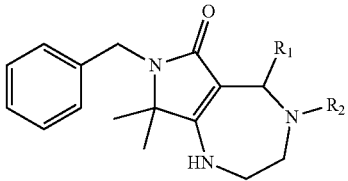
8a-y
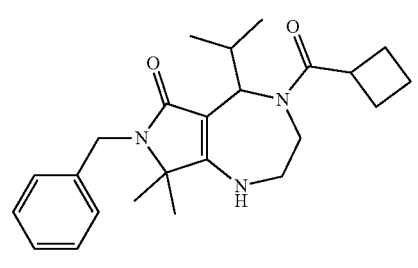
8b
33%
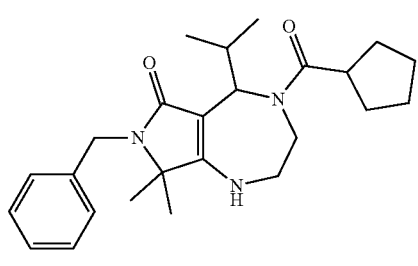
8c
18%
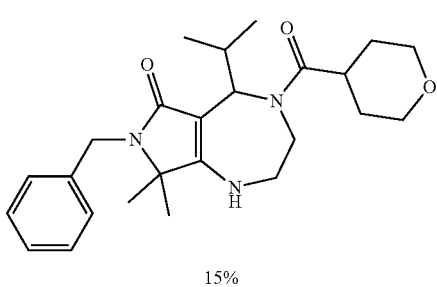 [SMILES: CC(C)C1C2=C(NCCN1C(=O)C1CCOCC1)C(C)(C)N(Cc1ccccc1)C2=O]
8d
15%
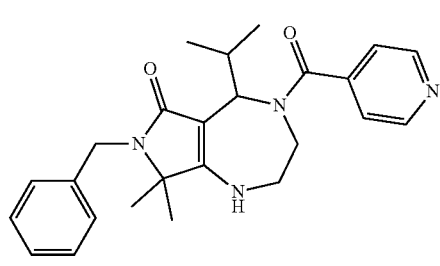
8e
30%
TABLE 1-continued
Synthesis of bicyclic pyrrolodiazepines
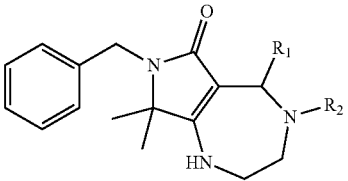
8a-y
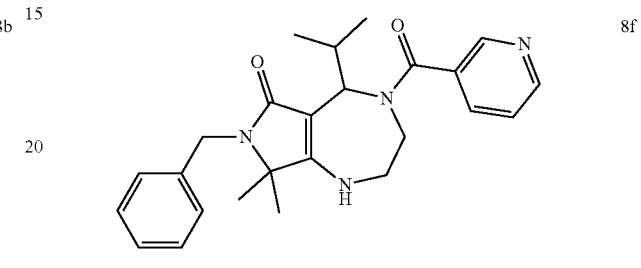
8f
18%
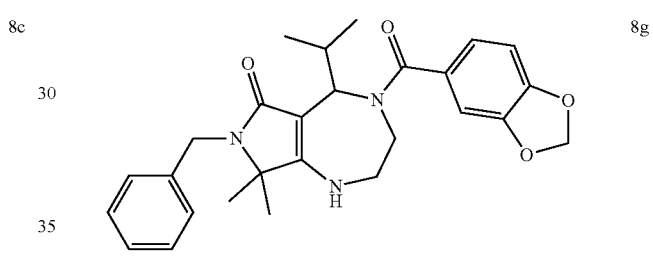
8g
18%
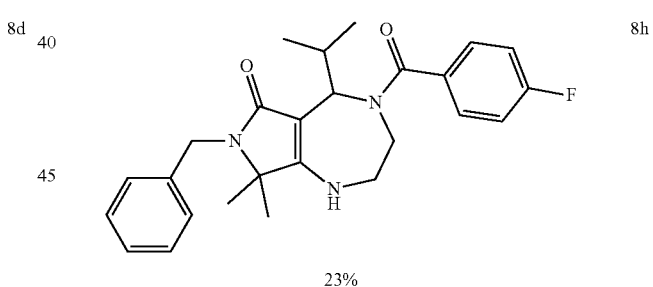
8h
23%
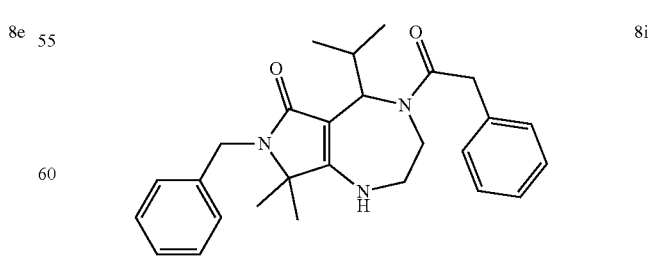
8i
36%

TABLE 1-continued
Synthesis of bicyclic pyrrolodiazepines
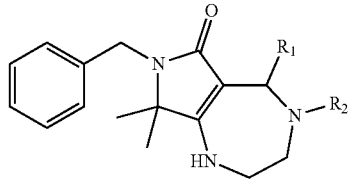
8a-y
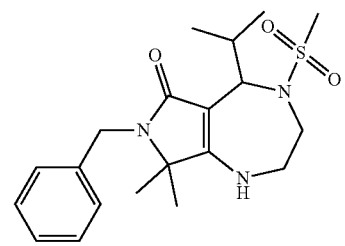
8j
66%
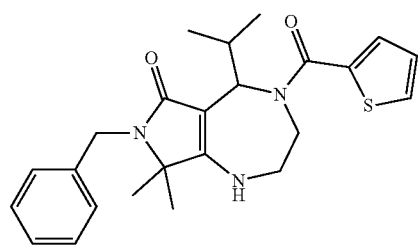
8k
68%
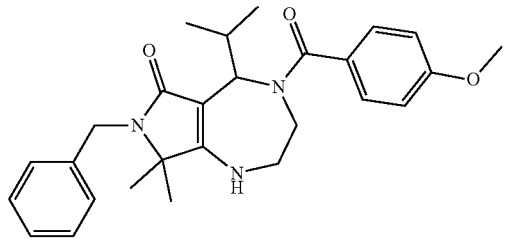
8l
42%
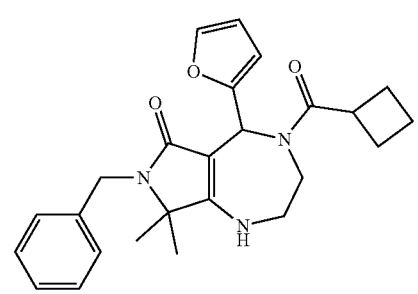
8m
41%
TABLE 1-continued
Synthesis of bicyclic pyrrolodiazepines
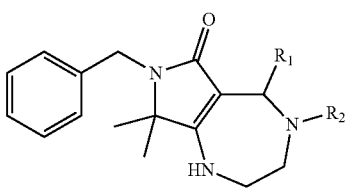
8a-y
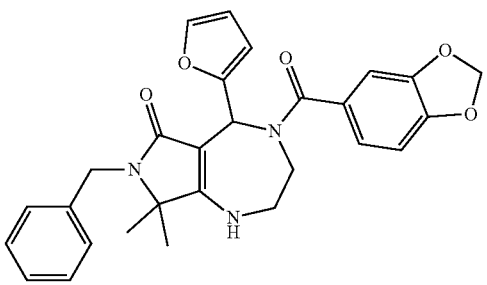
8n:
25%
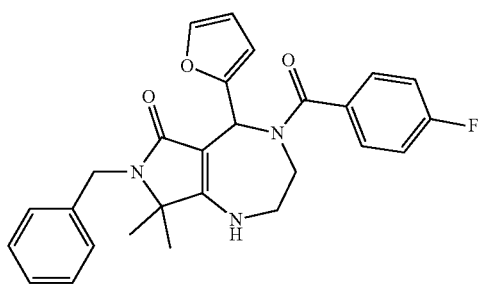
8o
32%
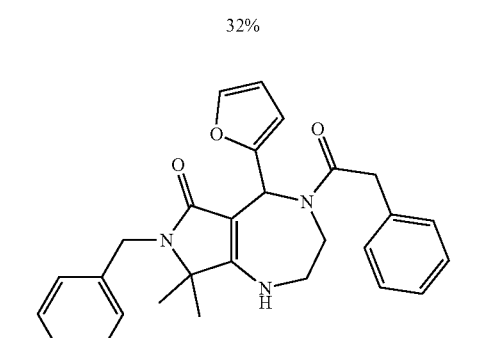
8p
37%
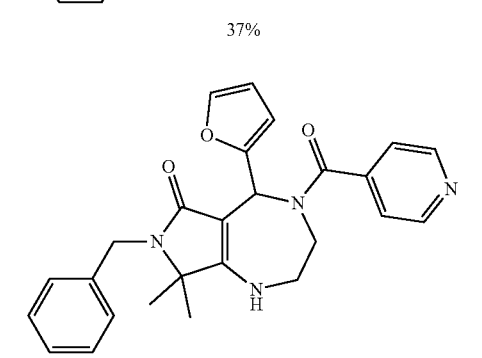
8q
41%

TABLE 1-continued

Synthesis of bicyclic pyrrolodiazepines

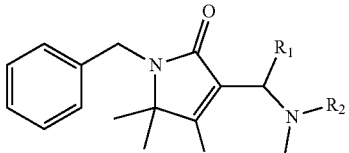

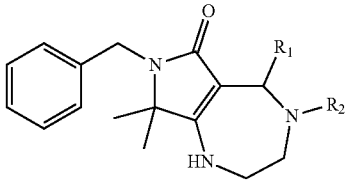

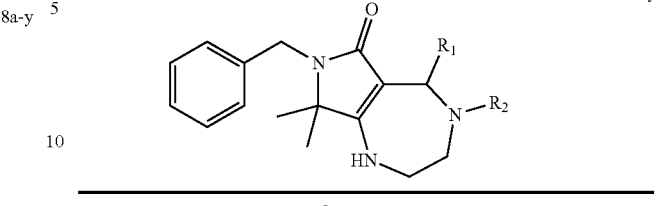

25%

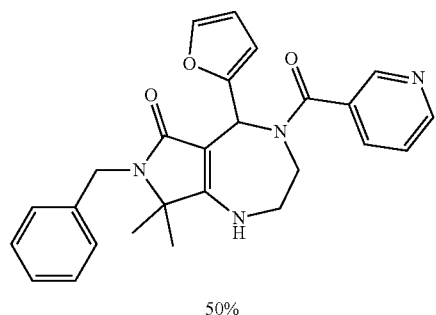 [SMILES: CC1(C)C2=C(C(=O)N1Cc1ccccc1)C(c1ccco1)N(C(=O)c1cccnc1)CCN2]

50%

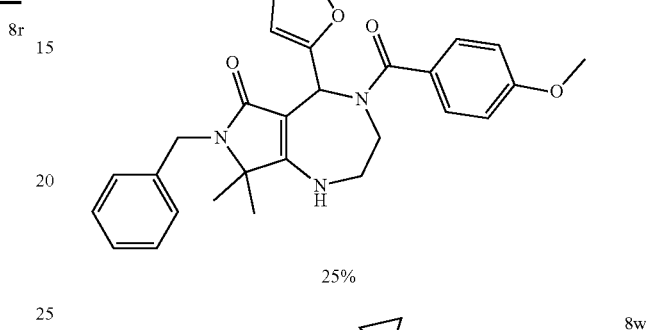

19%

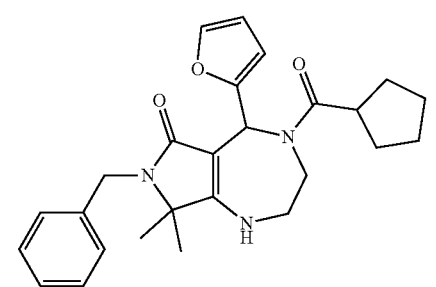

39%

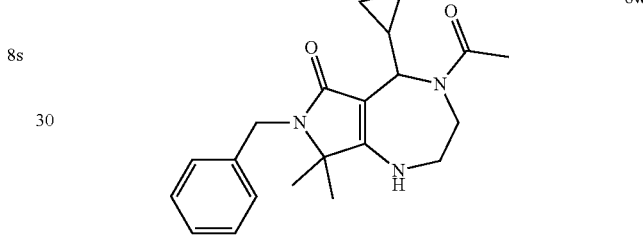

19%

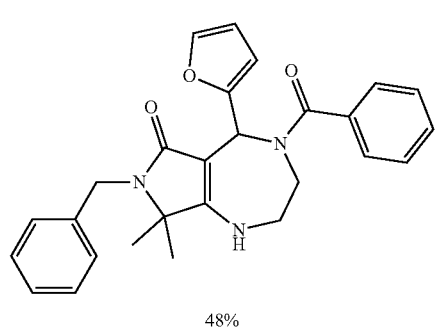 [SMILES: CC1(C)C2=C(C(=O)N1Cc1ccccc1)C(c1ccco1)N(C(=O)c1ccccc1)CCN2]

48%

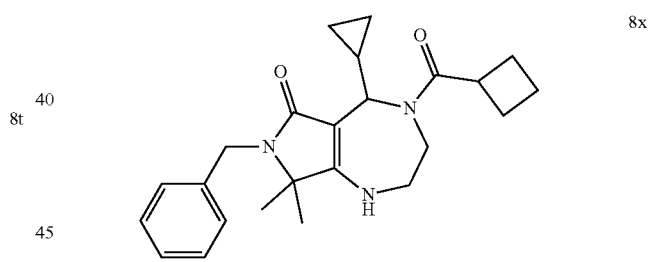

19%

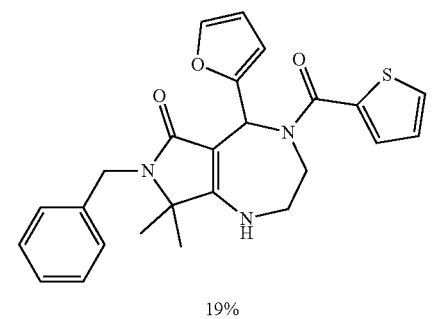 [SMILES: CC1(C)C2=C(C(=O)N1Cc1ccccc1)C(c1ccco1)N(C(=O)c1cccs1)CCN2]

19%

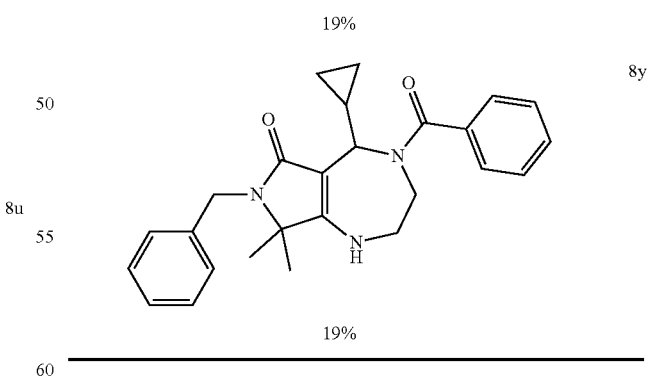

A subset of the compound library was submitted to the National Cancer Institute (NCI) for screening in their NCI60 panel for anti-cancer activity.[15-17] Assay details are provided in the supplemental. Notably, compound 8f was found to reduce cell growth of A549 non-small cell lung cancer cells by 32% at a concentration of 10 μM. Compounds 8c and 8m each reduced of A549 cell growth by 24% at 10 μM. While the potency is less than optimal, we anticipate that the general synthetic route will facilitate further optimization and exploration of these polycyclic scaffolds.

DISCUSSION

The diazepine and tetramic acid rings have proven to be privileged structures in biology and medicinal chemistry; however, there are remarkably few reports of heterocyclic scaffolds containing these two ring systems fused together. Here we report an efficient synthesis of a series of novel fused bicyclic heterocycles incorporating these motifs. The synthesis allows for extensive diversification of substituents on the unique 5,6-fused pyrrolodiazepinone ring system. We have demonstrated that this chemistry is wide in scope and can allow access to a large number of structurally diverse analogs. Yields for the final two-step sequence which allows wide diversification were highly variable and ranged from low (15% for 8d) to good (68% for 8k). There was no obvious pattern which explained the wide-ranging yields. However, it was observed that many of the final acylation reactions produced a large number of impurities (as assessed by LC/MS). As the intermediate free amines (7a-c) showed degradation to normal phase flash chromatography, it is possible that some of the amine degraded before the final acylation reaction, resulting in lower yields. Also, acylation of compounds 7a-c is likely not entirely chemoselective. For instance, besides the desired path to final compounds 8, the intermediate 7a-c has another amine and an enamine-like motif, both of which could contribute to impurities.

New potential drug targets are constantly being uncovered in the search for ways to treat existing diseases. In particular, there is increasing interest in developing small molecules that can modulate protein-protein[18-19] and protein-DNA/RNA[20-21] interactions. However, reliance on existing molecular space to pursue these challenging targets has led to frustratingly little success in the development of drugs against new target classes. One reason for this is that current compound libraries that are used for high-throughput screening and which define the chemotypes pursued in subsequent lead optimization cover very little chemical space.[22] In addition, they often over-represent scaffolds with highly aromatic and flat structures which may be unsuitable for targeting new types of drug targets.[1] Many of the new fused heterocycles we describe in this report have very high fractions of sp$^a$ (Fsp$^3$) character. For example, compound 8e has very favorable physiochemical properties, with a Fsp$^3$=0.56 and a CLogP=3.1.[14] Future efforts that replace the 7-benzyl group with other less hydrophobic groups would enable the generation of even more diverse structures with lower CLogP values and potentially higher Fsp$^3$ and solubility. Given the unique nature of this fused scaffold, the privileged structural character from which it was derived, and its highly 3-dimensional architecture, this may be a useful chemotype for many current and future drug discovery efforts.

To demonstrate the utility of this drug-like scaffold, several library members were screened in the NCI-60 cell line panel to identify anti-cancer activity.[15-17] Four compounds were chosen that represented a diverse spectrum of structures: 8e, 8f, 8i, and 8m. These compounds had both aryl and alkyl groups at C-5, and at N-5, they had small cycloalkyl and heteroaryl groups, thereby providing reasonable chemical space coverage from this set of available compounds. Notably, compound 8f showed significant cytotoxicity against the non-small cell lung cancer line A549. Cell proliferation was reduced 32% at a single concentration of 10 µM. In addition, compounds 8c and 8m also showed substantial cell growth inhibition as each reduced viability of A549 cells by 24% at 10 µM. Compound 8e had essentially no effect on the proliferation of A549 cells (<5% growth reduction). These results are especially significant since these three compounds are all closely structurally-related members of this drug-like bicylic system. This strongly suggests that these compounds share a common molecular target that may be exploitable for future development as a new anti-cancer strategy.

In conclusion, we have described the synthesis of a library of novel fused heterocyclic compounds. We expect that the synthetic routes we have described will allow the generation of many new diverse molecules from these potentially bioactive chemotypes. These molecules will enable chemical biology and drug discovery researchers to expand into new chemical space and explore new avenues for both basic and translational research.

GENERAL EXPERIMENTAL

All chemical reagents were obtained from commercial suppliers and used without further purification unless otherwise stated. Anhydrous solvents were purchased from Sigma-Aldrich, and dried over 3 Å molecular sieves when necessary. DCM and THF were purified by passage through a bed of activated alumina. Normal phase flash column chromatography was performed using Biotage KP-Sil 50 µm silica gel columns and ACS grade solvents on a Biotage Isolera flash purification system. Analytical thin layer chromatography (TLC) was performed on EM Reagent 0.25 mm silica gel 60 $F_{254}$ plates and visualized by UV light. Liquid chromatography/mass spectrometry (LCMS) was performed on a Waters Acquity-H UPLC system with a 2.1 mm×50 mm, 1.7 µm, reversed phase BEH $C_{18}$ column and LCMS grade solvents. A gradient elution from 95% water+0.1% formic acid/5% acetonitrile+0.1% formic acid to 95% acetonitrile+0.1% formic acid/5% water+0.1% formic acid over 2 min plus a further minute continuing this mixture at a flow rate of 0.85 mL/min was used as the eluent. Total ion current traces were obtained for electrospray positive and negative ionization (ESI+/ESI−). Proton ($^1$H), and carbon ($^{13}$C) NMR spectra were recorded on a Bruker Avance III w/ direct cryoprobe spectrometer. Chemical shifts were reported in ppm (δ) and were referenced using residual non-deuterated solvent as an internal standard (CDCl$_3$ at 7.26 ppm for $^1$H-NMR and 77.16 for $^{13}$C-NMR). The chemical shifts for $^1$H NMR and $^{13}$C NMR are reported to the second decimal place. Proton coupling constants are expressed in hertz (Hz). The following abbreviations were used to denote spin multiplicity for proton NMR: s=singlet, d=doublet, t=triplet, q=quartet, m=multiplet, brs=broad singlet, dd=doublet of doublets, dt=doublet of triplets, quin=quintet, tt=triplet of triplets. In some cases, overlapping signals occurred in the $^{13}$C NMR spectra.

Procedures and Analytical Data for the Synthesis of Compounds 2-8

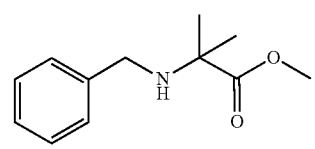

Methyl 2-(benzylamino)-2-methylpropanoate (2)

To a solution of methyl 2-amino-2-methylpropanoate hydrochloride 1 (503 mg, 3.27 mmol) in THF (5 ml) was added $MgSO_4$ (300 mg, 3.27 mmol), TEA (0.456 ml, 3.27 mmol), and benzaldehyde (0.33 ml, 3.27 mmol). The suspension was stirred at room temperature overnight. The reaction suspension was filtered, washed with THF, and the filtrate concentrated in vacuo. The residue obtained was taken up in MeOH (10 ml) and cooled to 0° C. $NaBH_4$ (149 mg, 3.93 mmol) was added in several portions over a period of 10 minutes. After the addition was complete, the reaction was warmed to room temperature and stirred for 1 h. Water was added and the product was extracted with EtOAc. The organic layer was combined, washed with brine, dried over anhydrous $Na_2SO_4$, filtered, and concentrated in vacuo to afford compound 2 (620 mg, 98%) which was used in the next step without further purification. $^1$H NMR (500 MHz, $CDCl_3$) δ 1.34-1.41 (m, 6H), 3.62 (br. s., 2H), 3.74 (br. s., 3H), 4.69 (br. s., 1H), 7.32-7.39 (m, 5H).

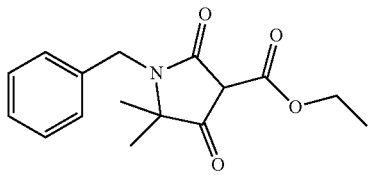 [SMILES: CCOC(=O)C1C(=O)N(Cc2ccccc2)C(C)(C)C1=O]

Ethyl 1-benzyl-5,5-dimethyl-2,4-dioxopyrrolidine-3-carboxylate (3)

A solution of methyl 2-(benzylamino)-2-methylpropanoate 2 (3.4 g, 16.4 mmol) in DCM (60 ml) was cooled to 0° C. and treated with TEA (5.03 ml, 36.1 mmol). To this was added a solution of ethyl 3-chloro-3-oxopropanoate (2.1 ml, 16.4 mmol) in 30 mL DCM dropwise. The reaction was stirred at room temperature for 6 h. Water was added and the layers were separated. The organic layer was washed with saturated aqueous $NaHCO_3$, 1N HCl and brine, then dried over anhydrous $Na_2SO_4$, filtered and concentrated in vacuo to give an oily residue (mixture of uncyclized intermediate and cyclized product). The residue was dissolved in MeOH (6 mL) and treated with sodium methoxide (1.26 g, 23.34 mmol). The resulting mixture was heated at 60° C. for 1 h. The reaction was then cooled to room temperature and quenched with water. DCM was added and the layers separated. The organic layer was washed with 1N HCl and water, then dried over anhydrous $Na_2SO_4$ and evaporated to yield compound 3 as an off-white solid (1.6 g, 60%). MS (ESI): mass calcd. for $C_{16}H_{19}NO_4$, 289.14; m/z found, 290.14 [M+H]$^+$; $^1$H NMR (500 MHz, $CDCl_3$) δ 1.27 (s, 6H), 1.42 (t, J=7.02 Hz, 3H), 4.42 (d, J=7.32 Hz, 2H), 4.56 (s, 2H), 7.23 (br. s., 1H), 7.29-7.35 (m, 4H).\

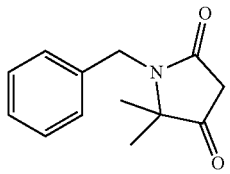 [SMILES: CC1(C)C(=O)CC(=O)N1Cc1ccccc1]

1-Benzyl-5,5-dimethylpyrrolidine-2,4-dione (4)

A mixture of ethyl 1-benzyl-5,5-dimethyl-2,4-dioxopyrrolidine-3-carboxylate 3 (0.52 g, 1.8 mmol), water (10 ml) and acetic acid (1 ml) was heated at 60° C. for 1 h. The reaction was cooled to room temperatue and extracted with DCM. The organic layer was washed with water, then dried over anhydrous Na2SO4, filtered and concentrated in vacuo to afford compound 4 as a pale-yellow solid (320 mg, 82%). MS (ESI): mass calcd. for $C_{13}H_{15}NO_2$, 217.11; m/z found, 218.13 [M+H]$^+$; $^1$H NMR (500 MHz, $CDCl_3$) δ 1.22 (s, 6H), 3.16 (s, 2H), 4.61 (s, 2H), 7.26-7.40 (m, 5H).

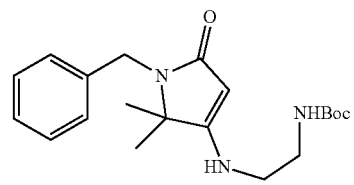 [SMILES: CC(C)(C)OC(=O)NCCNC1=CC(=O)N(Cc2ccccc2)C1(C)C]

tert-Butyl (2-((1-benzyl-2,2-dimethyl-5-oxo-2,5-dihydro-1H-pyrrol-3-yl)amino)ethyl)carbamate (5)

To a solution of 1-benzyl-5,5-dimethylpyrrolidine-2,4-dione 4 (500 mg, 2.301 mmol) and tert-butyl (2-aminoethyl) carbamate (369 mg, 2.301 mmol) in benzene (12 ml) was added 4-methylbenzenesulfonic acid hydrate (43.8 mg, 0.230 mmol). The resulting solution was heated to 80° C. and stirred at that temperature for 1 h. The solvents were removed in vacuo and the resulting residue was purified by flash chromatography on silica gel (0-10% MeOH in DCM) to afford compound 5 as a light pink solid (686 mg, 82%). MS (ESI): mass calcd. for $C_{20}H_{29}N_3O_3$, 359.22; m/z found, 360.28 [M+H]+; $^1$H NMR (500 MHz, $CDCl_3$) δ 1.15 (s, 6H), 1.41 (s, 9H), 3.11-3.17 (m, 2H), 3.37-3.44 (m, 2H), 4.54 (s, 2H), 4.66 (s, 1H), 4.90 (br. s., 1H), 5.40 (br. s., 1H), 7.17-7.23 (m, 2H), 7.28-7.32 (m, 3H).

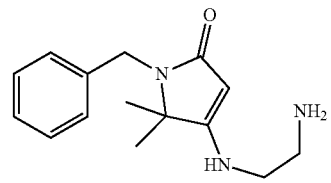 [SMILES: CC1(C)C(NCCN)=CC(=O)N1Cc1ccccc1]

4-((2-Aminoethyl)amino)-1-benzyl-5,5-dimethyl-1H-pyrrol-2(5H),-one (6)

Trifluoroacetic acid (1 ml) was added to a solution of tert-butyl (24(1-benzyl-2,2-dimethyl-5-oxo-2,5-dihydro-1H-pyrrol-3-yl)amino)ethyl)carbamate 5 (0.45 g, 1.25 mmol) in DCM (6 ml). The resulting solution was stirred at room temperature for 1 h. The solvents were evaporated under reduced pressure and the resulting residue was dried under high vacuum to yield vinylogous urea 6 (300 mg, 92%) which was taken to the next step without further purification. MS (ESI): mass calcd. for $C_{15}H_{21}N_3O$, 259.17; m/z found, 260.20 [M+H]+; $^1$H NMR (500 MHz, $CDCl_3$) δ 1.22 (s, 6H), 3.16 (s, 2H), 4.62 (s, 2H), 7.21 (s, 1H), 7.30-7.34 (m, 5H).

General Procedure a for the Synthesis of Bicyclic Amines 7a and 7b

To a solution of 4-((2-aminoethyl)amino)-1-benzyl-5,5-dimethyl-1H-pyrrol-2(5H),-one 6 (1.0 equiv) in ethanol (0.1 M) was added the respective aldehyde (1.1 equiv). Acetic acid (1.1 equiv) was added and the resulting clear solution was stirred at room temperature for 16 h. The mixture was concentrated in vacuo to give the respective bicylic amines (7a-7d) which were subsequently used without any purification.

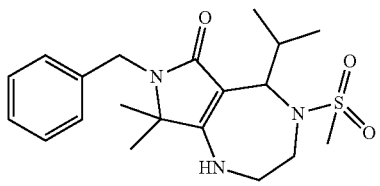 [SMILES: CC(C)C1C2=C(NCCN1S(C)(=O)=O)C(C)(C)N(Cc1ccccc1)C2=O]

7-benzyl-5-isopropyl-8,8-dimethyl-4-(methylsulfonyl)-2,3,4,5,7,8-hexahydropyrrolo[3,4-e][1,4]diazepin-6(1H)-one (8j)

Prepared according to a slightly modified version of General procedure B using 7-benzyl-5-isopropyl-8,8-dimethyl-2,3,4,5,7,8-hexahydropyrrolo[3,4-e][1,4]diazepin-6(1H),-one 7a. Instead of using an acid chloride, 1 eq. of methanesulfonyl chloride was used to afford 7-benzyl-5-isopropyl-8,8-dimethyl-4-(methylsulfonyl)-2,3,4,5,7,8-hexahydropyrrolo[3,4-e][1,4] diazepin-6(1H)-one 8j (66%). MS (ESI): mass calcd. for $C_{20}H_{29}N_3O_3S$, 391.19; m/z found, 392.31 [M+H]+; $^1$H NMR (500 MHz, CDCl$_3$) δ 1.05 (d, J=6.71 Hz, 3H) 1.10 (s, 10H) 1.12 (s, 5H) 1.18 (s, 4H) 1.99-2.09 (m, 1H) 2.85 (s, 3H) 3.29-3.38 (m, 1H) 3.48-3.58 (m, 3H) 3.96-4.05 (m, 3H) 4.38-4.46 (m, 1H) 4.46-4.51 (m, 1H) 4.67-4.73 (m, 1H) 7.21-7.25 (m, 3H) 7.29 (d, J=4.27 Hz, 5H); $^{13}$C NMR (126 MHz, CDCl$_3$) δ 19.90, 20.33, 24.69, 24.94, 34.02, 39.70, 42.48, 45.92, 46.44, 58.47, 61.23, 104.26, 127.18, 127.73, 128.58, 139.87, 164.13, 170.49.

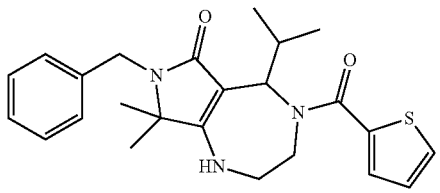 [SMILES: CC(C)C1C2=C(NCCN1C(=O)c1cccs1)C(C)(C)N(Cc1ccccc1)C2=O]

7-benzyl-5-isopropyl-8,8-dimethyl-4-(thiophene-2-carbonyl)-2,3,4,5,7,8-hexahydropyrrolo[3,4-e][1,4] diazepin-6(1H)-one (8k)

Prepared according to General procedure B using 7-benzyl-5-isopropyl-8,8-dimethyl-2,3,4,5,7,8-hexahydropyrrolo[3,4-e][1,4]diazepin-6(1H),-one 7a to afford 7-benzyl-5-isopropyl-8,8-dimethyl-4-(2-phenylacetyl)-2,3,4,5,7,8-hexahydropyrrolo[3,4-e] [1,4] diazepin-6(1H),-one 8k (68%). MS (ESI): mass calcd. for $C_{24}H_{29}N_3O_2S$, 423.20; m/z found, 424.32 [M+H]+; $^1$H NMR (500 MHz, CDCl$_3$) δ ppm 0.92 (d, J=6.10 Hz, 5H) 1.01 (d, J=6.10 Hz, 5H) 1.15 (s, 6H) 1.21 (s, 3H) 2.16 (d, J=8.24 Hz, 2H) 3.32 (t, J=12.51 Hz, 4H) 3.57 (br. s., 2H) 4.10 (br. s., 1H) 4.45 (d, J=15.56 Hz, 1H) 4.71 (d, J=16.17 Hz, 2H) 4.74-4.79 (m, 1H) 5.07 (d, J=9.77 Hz, 1H) 7.09 (br. s., 1H) 7.20-7.25 (m, 1H) 7.28-7.33 (m, 4H) 7.45 (d, J=5.19 Hz, 2H); $^{13}$C NMR (126 MHz, CDCl$_3$) δ 20.11, 20.16, 24.89, 24.97, 33.36, 42.44, 42.70, 46.90, 60.93, 61.50, 103.43, 127.11, 127.28, 127.71, 128.52, 128.91, 129.25, 137.81, 140.03, 164.63, 164.90, 170.47.

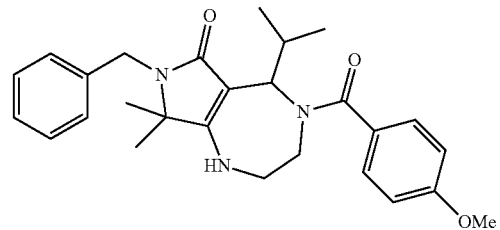 [SMILES: COc1ccc(C(=O)N2CCNC3=C(C(=O)N(Cc4ccccc4)C3(C)C)C2C(C)C)cc1]

7-benzyl-5-isopropyl-4-(4-methoxybenzoyl)-8,8-dimethyl-2,3,4,5,7,8-hexahydropyrrolo[3,4-e][1,4] diazepin-6(1H)-one (8l)

Prepared according to General procedure B using 7-benzyl-5-isopropyl-8,8-dimethyl-2,3,4,5,7,8-hexahydropyrrolo[3,4-e][1,4]diazepin-6(1H),-one 7a to afford 7-benzyl-4-(4-methoxybenzoyl)-8,8-dimethyl-2,3,4,5,7,8-hexahydropyrrolo[3,4-e] [1,4] diazepin-6(1H)-one 8l (42%). MS (ESI): mass calcd. for $C_{27}H_{33}N_3O_3$, 447.25; m/z found, 448.39 [M+H]+; $^1$H NMR (500 MHz, CDCl$_3$) δ ppm 0.87 (d, J=6.26 Hz, 3H) 0.92 (d, J=6.65 Hz, 3H) 1.16 (s, 3H) 1.22 (s, 3H) 2.03-2.16 (m, 1H) 3.21-3.30 (m, 1H) 3.31-3.40 (m, 1H) 3.56-3.65 (m, 1H) 3.84 (s, 3H) 4.07-4.13 (m, 1H) 4.45-4.49 (m, 0H) 4.52 (s, 1H) 4.61 (s, 1H) 4.65 (s, 1H) 4.74-4.83 (m, 1H) 6.92 (d, J=8.61 Hz, 2H) 7.23-7.26 (m, 1H) 7.29-7.35 (m, 4H); $^{13}$C NMR (126 MHz, CDCl$_3$) δ 19.94, 20.09, 25.00, 25.09, 33.48, 42.22, 42.45, 47.08, 55.41, 61.19, 61.30, 103.83, 113.95, 127.11, 127.79, 128.50, 128.89, 140.29, 160.80, 164.47, 170.21, 171.92.

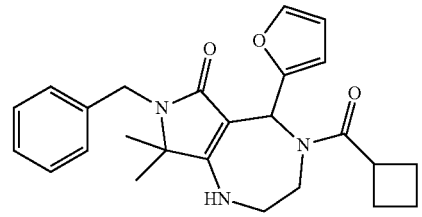 [SMILES: CC1(C)C2=C(C(=O)N1Cc1ccccc1)C(c1ccco1)N(C(=O)C1CCC1)CCN2]

7-benzyl-4-(cyclobutanecarbonyl)-5-(furan-2-yl)-8,8-dimethyl-2,3,4,5,7,8-hexahydropyrrolo[3,4-e][1,4] diazepin-6(1H)-one (8m)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b (61 mg, 0.15 mmol) to afford 7-benzyl-4-(cyclobutanecarbonyl)-5-(furan-2-yl)-8,8-dimethyl-2,3,4,5,7,8-hexahydropyrrolo[3,4-e][1,4]diazepin-6(1H)-one 8m (32 mg, 41%). MS (ESI): mass calcd. for $C_{25}H_{29}N_3O_3$, 419.22; m/z found, 420.34 [M+H]+; $^1$H NMR (500 MHz, CDCl$_3$) δ 1.18 (s, 3H) 1.21 (s, 3H) 1.78-1.91 (m, 1H) 1.95-2.09 (m, 1H) 2.23-2.41 (m, 3H) 2.47-2.61 (m, 1H) 2.87 (ddd, J=14.42, 10.60, 1.53 Hz, 1H) 3.31-3.39 (m, 1H) 3.41-3.48 (m, 1H) 3.65 (t, J=8.70 Hz, 1H) 4.24 (d, J=2.75

Hz, 1H) 4.28-4.36 (m, 1H) 4.46-4.55 (m, 1H) 4.59-4.66 (m, 1H) 6.02 (s, 1H) 6.05 (d, J=3.05 Hz, 1H) 6.29 (dd, J=3.05, 1.83 Hz, 1H) 7.21-7.26 (m, 1H) 7.30 (d, J=4.58 Hz, 4H) 7.36 (d, J=0.92 Hz, 1H); 13C NMR (126 MHz, CDCl$_3$) δ 17.86, 24.91, 25.08, 25.15, 25.55, 37.45, 41.72, 42.27, 46.86, 51.66, 61.78, 97.82, 108.54, 110.14, 127.02, 127.62, 128.42, 139.73, 142.63, 151.83, 163.20, 169.90, 173.78.

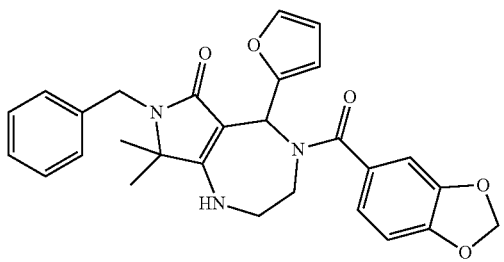 [SMILES: CC1(C)C2=C(C(=O)N1Cc1ccccc1)C(c1ccco1)N(C(=O)c1ccc3c(c1)OCO3)CCN2]

4-(benzo[d][1,3]dioxole-5-carbonyl)-7-benzyl-5-(furan-2-yl)-8,8-dimethyl-2,3,4,5,7,8-hexahydropyrrolo[3,4-e][1,4]diazepin-6(1H)-one (8n)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b to afford 4-(benzo[d][1,3]dioxole-5-carbonyl)-7-benzyl-5-(furan-2-yl)-8,8-dimethyl-2,3,4,5,7,8-hexahydropyrrolo[3,4-e][1,4]diazepin-6(1H)-one 8n (25%). MS (ESI): mass calcd. for $C_{28}H_{27}N_3O_5$, 485.20; m/z found, 486.29 [M+H]$^+$; $^1$H NMR (500 MHz, CDCl$_3$) δ ppm 1.20 (s, 5H) 1.22 (s, 4H) 3.05 (br. s., 1H) 3.54-3.57 (m, 2H) 4.19 (br. s., 1H) 4.44 (d, J=15.56 Hz, 2H) 4.60 (d, J=15.87 Hz, 1H) 5.99-6.03 (m, 2H) 6.06 (d, J=1.83 Hz, 1H) 6.22 (s, 1H) 6.30 (dd, J=3.36, 1.83 Hz, 1H) 6.85 (d, J=7.93 Hz, 1H) 7.17-7.24 (m, 3H) 7.29 (s, 4H) 7.42 (s, 1H); $^{13}$C NMR (126 MHz, CDCl$_3$) δ 24.92, 25.21, 29.84, 42.38, 42.66, 46.89, 54.54, 61.97, 97.37, 101.53, 108.52, 109.03, 110.35, 121.98, 127.13, 127.74, 128.53, 129.13, 139.93, 142.89, 147.79, 149.20, 152.14, 163.76, 169.74, 170.50.

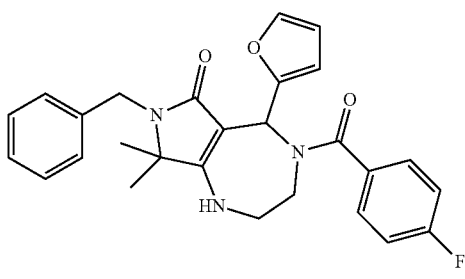 [SMILES: CC1(C)C2=C(C(=O)N1Cc1ccccc1)C(c1ccco1)N(C(=O)c1ccc(F)cc1)CCN2]

7-benzyl-4-(4-fluorobenzoyl)-5-(furan-2-yl)-8,8-dimethyl-2,3,4,5,7,8-hexahydropyrrolo[3,4-e][1,4]diazepin-6(1H)-one (8o)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b to afford 47-benzyl-4-(4-fluorobenzoyl)-5-(furan-2-yl)-8,8-dimethyl-2,3,4,5,7,8-hexahydropyrrolo[3,4-e][1,4]diazepin-6(1H)-one 8o (32%). MS (ESI): mass calcd. for $C_{27}H_{26}FN_3O_3$, 459.20; m/z found, 460.28 [M+H]$^+$; $^1$H NMR (500 MHz, CDCl$_3$) δ ppm 1.20 (s, 3H) 1.25 (s, 3H) 3.01-3.13 (m, 1H) 3.53-3.59 (m, 2H) 4.20 (br. s., 1H) 4.40 (d, J=15.87 Hz, 1H) 4.48 (d, J=15.26 Hz, 1H) 4.64 (d, J=15.87 Hz, 1H) 6.05 (d, J=3.36 Hz, 1H) 6.13 (s, 1H) 6.31 (dd, J=3.05, 1.83 Hz, 1H) 7.12-7.16 (m, 2H) 7.23 (d, J=4.58 Hz, 2H) 7.29 (br. s., 3H) 7.42 (s, 1H) 7.69 (d, J=5.49 Hz, 1H) 8.08-8.13 (m, 1H); $^{13}$C NMR (126 MHz, CDCl$_3$) δ ppm 25.12, 25.44, 42.49, 42.60, 47.13, 54.53, 61.98, 109.14, 110.45, 115.74, 115.84, 115.92, 116.01, 127.24, 127.87, 128.59, 129.78, 129.84, 132.96, 139.86, 143.01, 151.84, 163.42, 169.57.

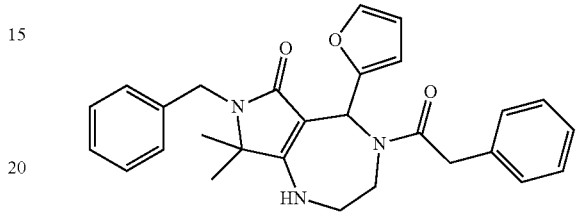

7-benzyl-5-(furan-2-yl)-8,8-dimethyl-4-(2-phenylacetyl)-2,3,4,5,7,8-hexahydropyrrolo[3,4-e][1,4]diazepin-6(1H)-one (8p)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b to afford 7-benzyl-5-(furan-2-yl)-8,8-dimethyl-4-(2-phenylacetyl)-2,3,4,5,7,8-hexahydropyrrolo[3,4-e][1,4]diazepin-6(1H)-one 8p (37%). MS (ESI): mass calcd. for $C_{28}H_{29}N_3O_3$, 455.22; m/z found, 456.29 [M+H]$^+$; $^1$H NMR (500 MHz, CDCl$_3$) δ ppm 1.05 (s, 3H) 1.20 (s, 3H) 2.87-2.98 (m, 1H) 3.32-3.41 (m, 1H) 3.43 (br. s., 1H) 3.99-4.03 (m, 1H) 4.04 (d, J=3.05 Hz, 1H) 4.06-4.12 (m, 1H) 4.35 (d, J=14.34 Hz, 1H) 4.47 (s, 1H) 4.56 (s, 1H) 5.96-6.02 (m, 1H) 6.26-6.30 (m, 2H) 7.28-7.31 (m, 7H) 7.34-7.37 (m, 3H); $^{13}$C NMR (126 MHz, CDCl$_3$) δ 24.90, 24.96, 41.00, 42.08, 42.34, 46.62, 53.03, 61.95, 96.54, 108.67, 110.35, 126.75, 127.14, 127.76, 128.48, 128.63, 129.37, 135.03, 139.79, 142.72, 151.92, 163.31, 169.86, 170.41.

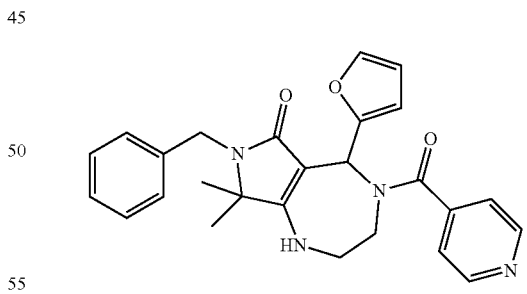

7-benzyl-5-(furan-2-yl)-4-isonicotinoyl-8,8-dimethyl-2,3,4,5,7,8-hexahydropyrrolo[3,4-e][1,4]diazepin-6(1H)-one (8q)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b to afford 7-benzyl-5-(furan-2-yl)-4-isonicotinoyl-8,8-dimethyl-2,3,4,5,7,8-hexahydropyrrolo[3,4-e] [1,4] diazepin-6(1H)-one 8q (37%). MS (ESI): mass calcd. for $C_{26}H_{26}N_4O_3$, 442.20; m/z found, 443.27 [M+H]+; 1H NMR (500 MHz, CDCl3) δ ppm 1.21 (s, 3H) 1.26 (s, 3H) 3.06-3.14 (m, 1H) 3.50-3.64 (m, 2H) 4.22-4.29 (m, 1H) 4.42 (s, 1H) 4.47-4.53 (m, 1H) 4.62-4.68 (m, 1H) 6.00 (s, 1H) 6.05-6.08 (m, 1H) 6.30-6.34 (m, 1H) 7.24-7.34 (m, 6H), 7.44 (d, J=1.83 Hz, 1H) 7.53-7.57 (m, 2H) 8.75 (d, J=5.80 Hz, 2H); 13C NMR (126 MHz, CDCl3) δ ppm 14.14, 22.68, 24.99, 25.35, 31.61, 42.26, 42.36, 46.89, 54.18, 61.89, 97.44, 109.21, 110.39, 121.47, 127.13, 127.75, 128.47, 139.64, 143.02, 150.39, 151.15, 152.50.

1.21-1.22 (m, 6H), 1.62-1.66 (m, 4H), 1.70-1.82 (m, 4H), 1.94-2.01 (m, 1H), 2.02-2.08 (m, 1H), 2.86-2.96 (m, 1H), 3.25-3.40 (m, 2H), 3.43-3.50 (m, 1H), 4.11-4.15 (m, 1H), 4.31-4.38 (m, 1H), 4.48-4.54 (m, 1H), 4.62-4.68 (m, 1H), 6.07-6.09 (m, 1H), 6.30-6.32 (m, 2H), 7.24-7.32 (m, 5H), 7.38 (s, 1H); 13C NMR (126 MHz, CDCl3) δ 25.10, 25.35, 26.26, 26.32, 30.48, 30.61, 41.52, 42.08, 42.50, 47.14, 52.20, 61.97, 98.07, 108.69, 110.32, 127.20, 127.83, 128.59, 139.90, 142.80, 152.24, 163.35, 170.06, 175.42.

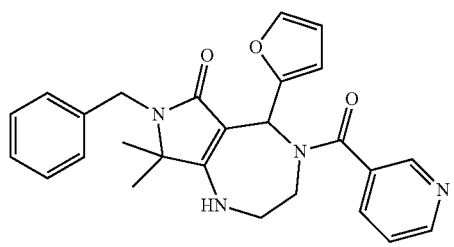 [SMILES: CC1(C)C2=C(C(=O)N1Cc1ccccc1)C(c1ccco1)N(C(=O)c1cccnc1)CCN2]

7-benzyl-5-(furan-2-yl)-8,8-dimethyl-4-nicotinoyl-2,3,4,5,7,8-hexahydropyrrolo[3,4-e][1,4]diazepin-6(1H)-one (8r)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b to afford 7-benzyl-5-(furan-2-yl)-8,8-dimethyl-4-nicotinoyl-2,3,4,5,7,8-hexahydropyrrolo[3,4-e] [1,4] diazepin-6(1H)-one 8r (50%). MS (ESI): mass calcd. for $C_{26}H_{26}N_4O_3$, 442.20; m/z found, 443.28 [M+H]+; 1H NMR (500 MHz, CDCl3) δ ppm 1.22 (s, 3H), 1.24 (s, 3H), 3.07-3.17 (m, 1H), 3.57-3.63 (m, 2H), 4.22-4.26 (m, 1H), 4.42-4.46 (m, 1H), 4.48-4.53 (m, 1H), 4.58-4.64 (m, 1H), 6.03-6.09 (m, 2H), 6.30-6.34 (m, 1H), 7.20-7.30 (m, 3H), 7.38-7.45 (m, 2H), 8.01-8.06 (m, 1H), 8.68-8.72 (m, 1H), 8.91-8.96 (m, 1H); 13C NMR (126 MHz, CDCl3) δ 24.82, 25.17, 42.36, 42.56, 46.72, 54.53, 62.15, 96.20, 109.28, 110.46, 123.56, 127.18, 127.65, 128.55, 131.70, 135.12, 139.67, 143.09, 148.35, 150.82, 151.51, 164.10, 168.37, 169.64.

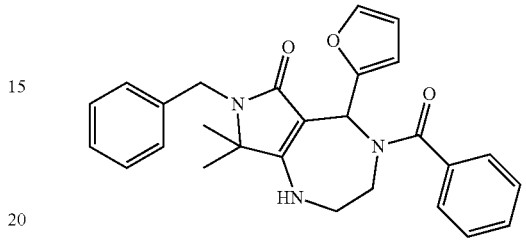

4-benzoyl-7-benzyl-5-(furan-2-yl)-8,8-dimethyl-2,3,4,5,7,8-hexahydropyrrolo[3,4-e][1,4]diazepin-6(1H)-one (8t)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b (61 mg, 0.18 mmol) to afford 4-benzoyl-7-benzyl-5-(furan-2-yl)-8,8-dimethyl-2,3,4,5,7,8-hexahydropyrrolo[3,4-e][1,4]diazepin-6(1H)-one 8t (39 mg, 48%). MS (ESI): mass calcd. for $C_{27}H_{27}N_3O_3$, 441.21; m/z found, 442.27 [M+H]+; 1H NMR (500 MHz, CDCl3) δ 1.15-1.18 (m, 3H) 1.21 (s, 3H) 3.04 (ddd, J=14.50, 7.93, 4.12 Hz, 1H) 3.46-3.56 (m, 2H) 4.39 (d, J=15.87 Hz, 1H) 4.44 (br. s., 1H) 4.46-4.52 (m, 1H) 4.63 (d, J=15.87 Hz, 1H) 6.04 (d, J=3.05 Hz, 1H) 6.13 (s, 1H) 6.30 (dd, J=3.05, 1.83 Hz, 1H) 7.20-7.26 (m, 1H) 7.27-7.32 (m, 4H) 7.40-7.46 (m, 5H) 7.58-7.68 (m, 2H); 13C NMR (126 MHz, CDCl3) δ 24.89, 25.21, 42.23, 46.91, 54.28, 61.78, 97.47, 108.83, 110.19, 127.00, 127.15, 127.63, 128.38, 130.02, 125.33, 139.78, 142.75, 151.86, 163.29, 169.46, 170.95.

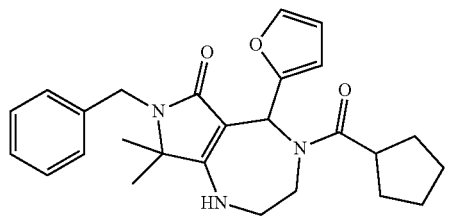 [SMILES: CC1(C)C2=C(C(=O)N1Cc1ccccc1)C(c1ccco1)N(C(=O)C1CCCC1)CCN2]

7-benzyl-4-(cyclopentanecarbonyl)-5-(furan-2-yl)-8,8-dimethyl-2,3,4,5,7,8-hexahydropyrrolo[3,4-e][1,4]diazepin-6(1H)-one (8s)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b to afford 7-benzyl-4-(cyclopentanecarbonyl)-5-(furan-2-yl)-8,8-dimethyl-2,3,4,5,7,8-hexahydropyrrolo[3,4-e][1,4]diazepin-6(1H)-one 8s (39%). MS (ESI): mass calcd. for $C_{26}H_{31}N_3O_3$, 433.24; m/z found, 434.33 [M+H]+; 1H NMR (500 MHz, CDCl3) δ ppm

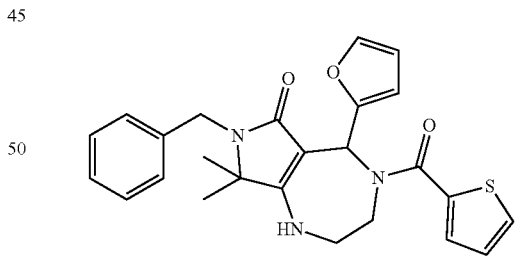

7-benzyl-5-(furan-2-yl)-8,8-dimethyl-4-(thiophene-2-carbonyl)-2,3,4,5,7,8-hexahydropyrrolo[3,4-e][1,4]diazepin-6(1H)-one (8u)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b (12 mg, 0.035 mmol) to afford 7-benzyl-5-(furan-2-yl)-8,8-dimethyl-4-(thiophene-2-carbonyl)-2,3,4,5,7,8-hexahydropyrrolo[3,4-e][1,4]diazepin-6(1H)-one 8u (3 mg, 19%). MS (ESI): mass calcd. for $C_{25}H_{25}N_3O_3S$, 447.16; m/z found, 448.27

[M+H]⁺; ¹H NMR (500 MHz, CDCl₃) δ 1.19-1.24 (m, 6H) 3.07-3.18 (m, 1H) 3.46-3.52 (m, 2H) 3.54-3.61 (m, 2H) 3.66-3.72 (m, 1H) 4.23 (br. s., 1H) 4.36-4.41 (m, 1H) 4.46 (d, J=16.04 Hz, 1H) 4.62 (s, 1H) 6.14 (br. s., 1H) 6.34 (dd, J=3.13, 1.96 Hz, 1H) 6.68 (br. s., 1H) 7.06-7.12 (m, 1H) 7.20-7.26 (m, 2H) 7.28-7.32 (m, 3H) 7.44 (s, 1H) 7.49 (d, J=5.09 Hz, 1H) 7.79 (br. s., 1H); ¹³C NMR (126 MHz, CDCl₃) δ 25.01, 25.38, 42.45, 43.37, 46.95, 54.48, 62.00, 97.76, 109.11, 110.45, 127.18, 127.32, 127.81, 128.57, 129.49, 129.89, 137.26, 139.87, 142.99, 152.06, 163.35, 164.11, 169.78.

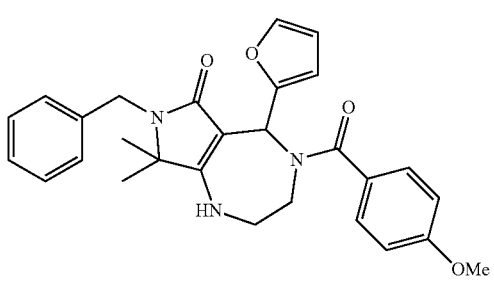 [SMILES: COc1ccc(C(=O)N2CCNC3=C(C(=O)N(Cc4ccccc4)C3(C)C)C2c2ccco2)cc1]

7-benzyl-5-(furan-2-yl)-4-(4-methoxybenzoyl)-8,8-dimethyl-2,3,4,5,7,8-hexahydropyrrolo[3,4-e][1,4]diazepin-6(1H)-one (8v)

Prepared according to General procedure B using 7-benzyl-5-(furan-2-yl)-8,8-dimethyl-2,3,4,5,7,8-hexahydropyrrolo[3,4-e][1,4]diazepin-6(1H),-one 7b to afford 7-benzyl-5-(furan-2-yl)-4-(4-methoxybenzoyl)-8,8-dimethyl-2,3,4,5,7,8-hexahydropyrrolo[3,4-e] [1,4] diazepin-6(1H)-one 8v (25%). MS (ESI): mass calcd. for C₂₈H₂₉N₃O₄, 471.22; m/z found, 472.35 [M+H]+; ¹H NMR (500 MHz, CDCl₃) δ 1.20 (s, 3H) 1.21-1.24 (m, 3H) 2.98-3.11 (m, 1H) 3.53-3.60 (m, 2H) 3.84 (s, 3H) 4.24 (br. s., 1H) 4.42 (d, J=15.65 Hz, 1H) 4.48 (d, J=15.26 Hz, 1H) 4.64 (d, J=15.65 Hz, 2H) 6.06 (d, J=3.13 Hz, 1H) 6.26 (s, 1H) 6.31 (dd, J=3.13, 1.96 Hz, 1H) 6.95 (d, J=8.61 Hz, 2H) 7.21-7.26 (m, 1H) 7.29 (d, J=4.70 Hz, 4H) 7.42 (s, 1H) 7.66 (d, J=9.00 Hz, 2H); ¹³C NMR (126 MHz, CDCl₃) δ 25.08, 25.41, 42.44, 42.65, 47.16, 54.59, 55.47, 61.91, 98.10, 108.97, 110.37, 114.08, 127.16, 127.59, 127.85, 128.55, 129.49, 139.98, 142.86, 152.26, 161.12, 163.37, 169.70, 170.98.

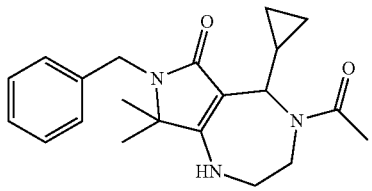 [SMILES: CC(=O)N1CCNC2=C(C(=O)N(Cc3ccccc3)C2(C)C)C1C1CC1]

4-acetyl-7-benzyl-5-cyclopropyl-8,8-dimethyl-2,3,4,5,7,8-hexahydropyrrolo[3,4-e][1,4]diazepin-6(1H)-one (8w)

Prepared according to General procedure B using 7-benzyl-5-cyclopropyl-8,8-dimethyl-2,3,4,5,7,8-hexahydropyrrolo[3,4-e][1,4]diazepin-6(1H)-one 7c to afford 74-acetyl-7-benzyl-5-cyclopropyl-8,8-dimethyl-2,3,4,5,7,8-hexahydropyrrolo[3,4-e] [1,4] diazepin-6(1H)-one 8w (19%). MS (ESI): mass calcd. for C₂₁H₂₇N₃O₂, 353.21; m/z found, 354.34 [M+H]+; ¹H NMR (500 MHz, CDCl₃) δ ppm 0.24-0.31 (m, 1H) 0.43-0.51 (m, 1H) 0.63-0.69 (m, 1H) 0.73 (dd, J=9.92, 5.04 Hz, 1H) 1.14 (s, 3H) 1.15 (s, 3H) 2.20 (s, 3H) 3.31 (d, J=12.21 Hz, 3H) 3.45-3.53 (m, 5H) 4.02 (br. s., 3H) 4.49-4.64 (m, 12H) 7.24 (dd, J=8.85, 4.27 Hz, 2H) 7.28-7.33 (m, 5H); ¹³C NMR (126 MHz, CDCl₃) δ 2.21, 5.23, 15.06, 22.18, 24.98, 25.15, 41.61, 42.48, 46.99, 57.88, 61.80, 100.23, 127.15, 127.69, 128.55, 139.74, 163.20, 169.87, 170.66.

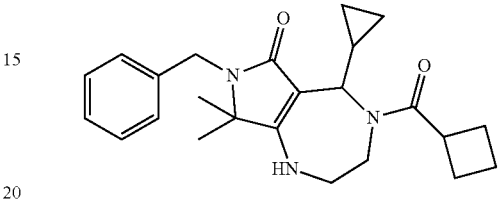

7-benzyl-4-(cyclobutanecarbonyl)-5-cyclopropyl-8,8-dimethyl-2,3,4,5,7,8-hexahydropyrrolo[3,4-e][1,4]diazepin-6(1H)-one (8x)

Prepared according to General procedure B using 7-benzyl-5-cyclopropyl-8,8-dimethyl-2,3,4,5,7,8-hexahydropyrrolo[3,4-e][1,4]diazepin-6(1H)-one 7c to afford 7-benzyl-4-(cyclobutanecarbonyl)-5-cyclopropyl-8,8-dimethyl-2,3,4,5,7,8-hexahydropyrrolo[3,4-e][1,4]diazepin-6(1H)-one 8x (10%). MS (ESI): mass calcd. for C₂₄H₃₁N₃O₂, 393.24; m/z found, 394.37 [M+H]+; ¹H NMR (500 MHz, CDCl₃) δ ppm 0.21-0.27 (m, 1H) 0.39-0.48 (m, 1H) 0.65 (d, J=2.74 Hz, 2H) 0.86 (d, J=19.96 Hz, 1H) 1.01-1.07 (m, 1H) 1.11 (s, 3H) 1.14 (s, 2H) 1.73-1.84 (m, 1H) 1.95-2.07 (m, 1H) 2.13-2.28 (m, 3H) 2.33-2.43 (m, 1H) 3.23-3.33 (m, 1H) 3.39 (s, 1H) 3.45-3.52 (m, 2H) 3.95-3.99 (m, 1H) 4.45-4.56 (m, 3H) 7.20-7.25 (m, 1H) 7.28-7.30 (m, 3H). ¹³C NMR (126 MHz, CDCl₃) δ 2.05, 5.22, 14.70, 17.96, 25.00, 25.07, 25.19, 25.72, 37.64, 41.57, 42.45, 47.04, 56.11, 61.66, 101.23, 127.12, 127.70, 128.55, 139.92, 163.12, 170.50, 173.70.

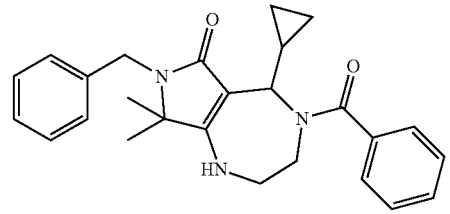 [SMILES: CC1(C)C2=C(C(=O)N1Cc1ccccc1)C(C1CC1)N(C(=O)c1ccccc1)CCN2]

4-benzoyl-7-benzyl-5-cyclopropyl-8,8-dimethyl-2,3,4,5,7,8-hexahydropyrrolo[3,4-e][1,4]diazepin-6(1H)-one (8y)

Prepared according to General procedure B using 7-benzyl-5-cyclopropyl-8,8-dimethyl-2,3,4,5,7,8-hexahydropyrrolo[3,4-e][1,4]diazepin-6(1H)-one 7c to afford 4-benzoyl-7-benzyl-5-cyclopropyl-8,8-dimethyl-2,3,4,5,7,8-hexahydropyrrolo[3,4-e] [1,4] diazepin-6(1H)-one 8y (19%). MS (ESI): mass calcd. for C₂₆H₂₉N₃O₂, 415.23; m/z found, 416.35 [M+H]+; ¹H NMR (500 MHz, CDCl₃) δ ppm 0.06-0.14 (m, 1H) 0.37-0.44 (m, 1H) 0.50-0.60 (m, 1H) 0.89 (s, 2H) 1.03-1.15 (m, 2H) 1.17 (s, 2H) 1.20 (s, 2H) 3.40-3.50

(m, 1H) 3.58-3.69 (m, 2H) 4.05-4.13 (m, 1H) 4.45-4.61 (m, 2H) 4.74-4.83 (m, 1H) 7.22-7.26 (m, 1H) 7.28-7.31 (m, 2H) 7.33-7.38 (m, 2H) 7.39-7.43 (m, 2H); $^{13}$C NMR (126 MHz, CDCl$_3$) δ 2.30, 5.10, 15.18, 24.95, 25.09, 41.86, 42.37, 47.06, 58.88, 61.75, 100.28, 126.59, 127.07, 127.60, 128.48, 128.70, 129.86, 136.01, 139.97, 163.99, 170.13, 170.82.

TABLE 2

| Synthesized Molecules and Compounds | | |
|---|---|---|
| Structure | Molecule Name | Compound ID |
| | | NUCC-0202791 |
| | | NUCC-0202790 |
| | | NUCC-0202789 |
| | | NUCC-0202788 |

TABLE 2-continued

Synthesized Molecules and Compounds

| Structure | Molecule Name | Compound ID |
|---|---|---|
| | | NUCC-0202787 |
| | | NUCC-0202786 |
| | | NUCC-0202785 |
| | | NUCC-0202784 |

TABLE 2-continued
Synthesized Molecules and Compounds
| Structure | Molecule Name | Compound ID |
|---|---|---|
| 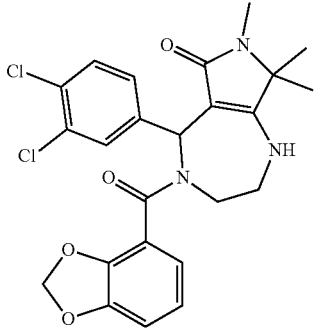 [SMILES: CN1C(=O)C2=C(NCCN(C(=O)c3cccc4c3OCO4)C2c2ccc(Cl)c(Cl)c2)C1(C)C] | | NUCC-0202783 |
| 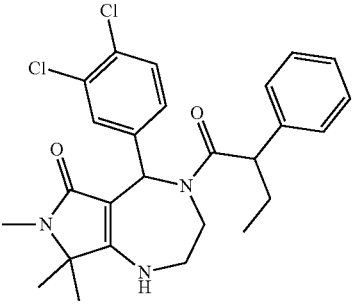 [SMILES: CCC(C(=O)N1CCNC2=C(C(=O)N(C)C2(C)C)C1c1ccc(Cl)c(Cl)c1)c1ccccc1] | | NUCC-0202782 |
| 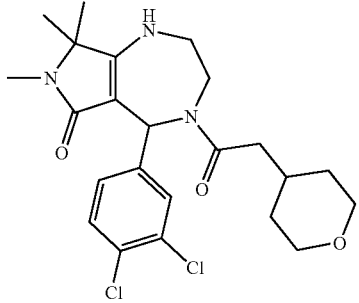 [SMILES: CN1C(=O)C2=C(NCCN(C(=O)CC3CCOCC3)C2c2ccc(Cl)c(Cl)c2)C1(C)C] | | NUCC-0202781 |
| 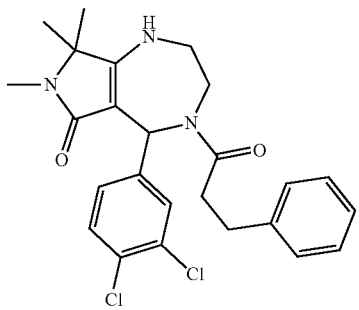 [SMILES: CN1C(=O)C2=C(NCCN(C(=O)CCc3ccccc3)C2c2ccc(Cl)c(Cl)c2)C1(C)C] | | NUCC-0202780 |

TABLE 2-continued

| Structure | Molecule Name | Compound ID |
|---|---|---|
| | | NUCC-0202779 |
| | | NUCC-0202778 |
| | | NUCC-0202777 |
| | | NUCC-0202776 |
| | | NUCC-0202775 |

TABLE 2-continued
Synthesized Molecules and Compounds
| Structure | Molecule Name Compound ID |
|---|---|
| 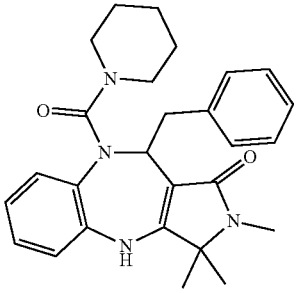 [SMILES: CN1C(=O)C2=C(Nc3ccccc3N(C(=O)N3CCCCC3)C2Cc2ccccc2)C1(C)C] | NUCC-0202774 |
| 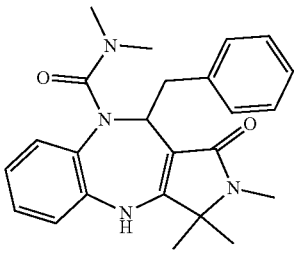 [SMILES: CN(C)C(=O)N1c2ccccc2NC2=C(C(=O)N(C)C2(C)C)C1Cc1ccccc1] | NUCC-0202773 |
| 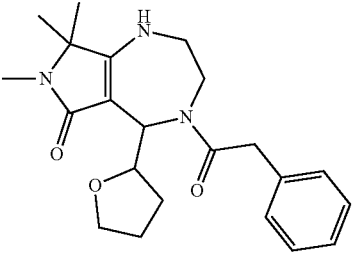 [SMILES: CN1C(=O)C2=C(NCCN(C(=O)Cc3ccccc3)C2C2CCCO2)C1(C)C] | NUCC-0202520 |
| 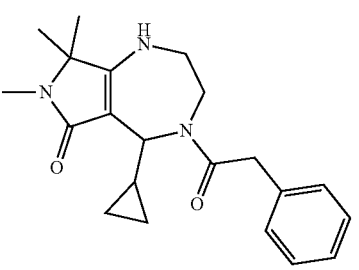 [SMILES: CN1C(=O)C2=C(NCCN(C(=O)Cc3ccccc3)C2C2CC2)C1(C)C] | NUCC-0202519 |
| 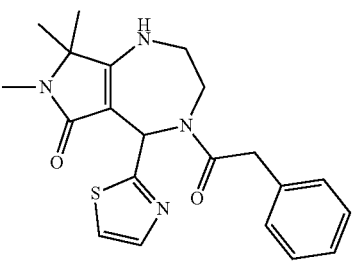 [SMILES: CN1C(=O)C2=C(NCCN(C(=O)Cc3ccccc3)C2c2nccs2)C1(C)C] | NUCC-0202518 |

TABLE 2-continued

Synthesized Molecules and Compounds

| Structure | Molecule Name Compound ID |
|---|---|
| 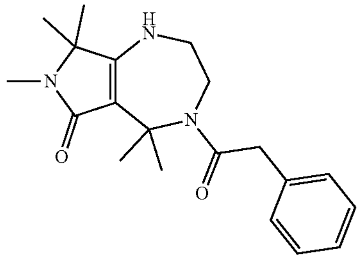 [SMILES: CN1C(=O)C2=C(NCCN(C(=O)Cc3ccccc3)C2(C)C)C1(C)C] | NUCC-0202517 |
| 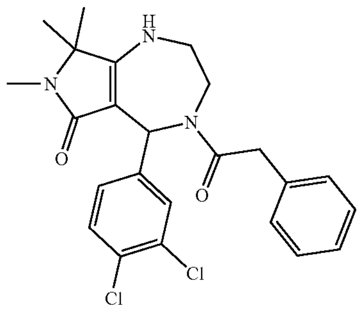 [SMILES: CN1C(=O)C2=C(NCCN(C(=O)Cc3ccccc3)C2c2ccc(Cl)c(Cl)c2)C1(C)C] | NUCC-0202516 |
| 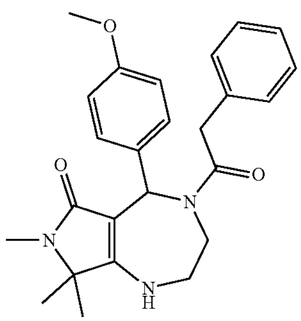 [SMILES: COc1ccc(C2C3=C(NCCN2C(=O)Cc2ccccc2)C(C)(C)N(C)C3=O)cc1] | NUCC-0202515 |
| 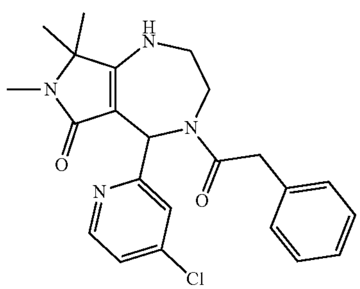 [SMILES: CN1C(=O)C2=C(NCCN(C(=O)Cc3ccccc3)C2c2cc(Cl)ccn2)C1(C)C] | NUCC-0202514 |
| 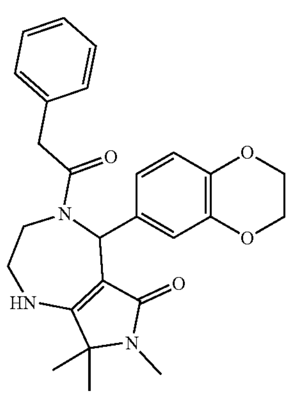 [SMILES: CN1C(=O)C2=C(NCCN(C(=O)Cc3ccccc3)C2c2ccc3c(c2)OCCO3)C1(C)C] | NUCC-0202513 |

TABLE 2-continued

Synthesized Molecules and Compounds

| Structure | Molecule Name | Compound ID |
|---|---|---|
| | | NUCC-0202512 |
| | | NUCC-0202511 |
| | | NUCC-0202510 |
| | | NUCC-0202509 |
| | | NUCC-0202508 |

TABLE 2-continued

Synthesized Molecules and Compounds

| Structure | Molecule Name | Compound ID |
|---|---|---|
| 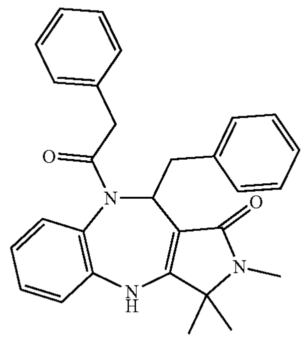 [SMILES: CN1C(=O)C2=C(Nc3ccccc3N(C(=O)Cc3ccccc3)C2Cc2ccccc2)C1(C)C] | NUCC-0202507 | |
| 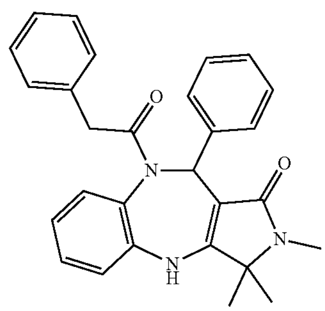 [SMILES: CN1C(=O)C2=C(Nc3ccccc3N(C(=O)Cc3ccccc3)C2c2ccccc2)C1(C)C] | NUCC-0202506 | |
| 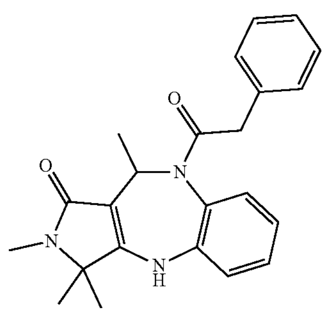 [SMILES: CC1C2=C(Nc3ccccc3N1C(=O)Cc1ccccc1)C(C)(C)N(C)C2=O] | NUCC-0202505 | |
| 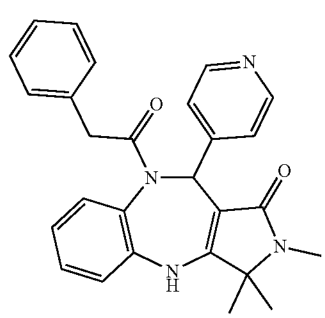 [SMILES: CN1C(=O)C2=C(Nc3ccccc3N(C(=O)Cc3ccccc3)C2c2ccncc2)C1(C)C] | NUCC-0202504 | |

TABLE 2-continued

Synthesized Molecules and Compounds

| Structure | Molecule Name Compound ID |
|---|---|
| 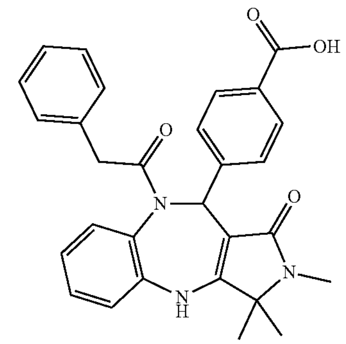 [SMILES: CN1C(=O)C2=C(Nc3ccccc3N(C(=O)Cc3ccccc3)C2c2ccc(C(=O)O)cc2)C1(C)C] | NUCC-0202503 |
| 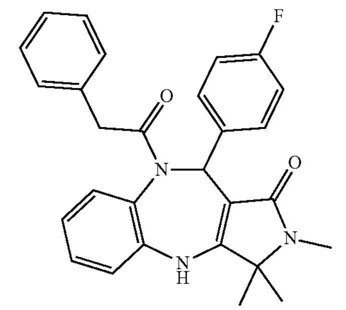 [SMILES: CN1C(=O)C2=C(Nc3ccccc3N(C(=O)Cc3ccccc3)C2c2ccc(F)cc2)C1(C)C] | NUCC-0202502 |
| 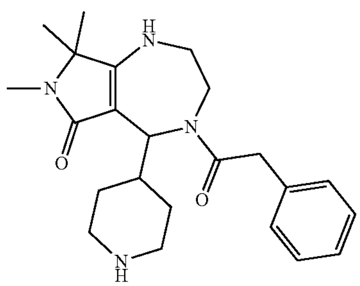 [SMILES: CN1C(=O)C2=C(NCCN(C(=O)Cc3ccccc3)C2C2CCNCC2)C1(C)C] | NUCC-0202501 |
| 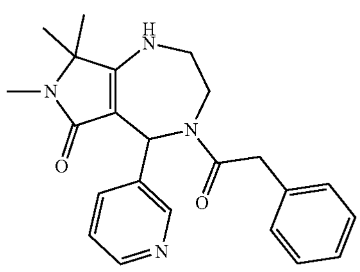 [SMILES: CN1C(=O)C2=C(NCCN(C(=O)Cc3ccccc3)C2c2cccnc2)C1(C)C] | NUCC-0202500 |
| 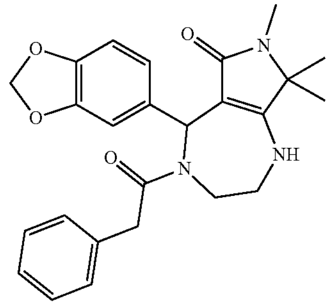 [SMILES: CN1C(=O)C2=C(NCCN(C(=O)Cc3ccccc3)C2c2ccc3c(c2)OCO3)C1(C)C] | NUCC-0202499 |

TABLE 2-continued

Synthesized Molecules and Compounds

| Structure | Molecule Name | Compound ID |
|---|---|---|
| | | NUCC-0202498 |
| | | NUCC-0202497 |
| | | NUCC-0202496 |
| | | NUCC-0202495 |
| | | NUCC-0202494 |

TABLE 2-continued

| Structure | Molecule Name | Compound ID |
|---|---|---|
| 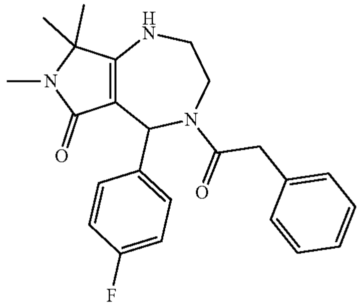 [SMILES: CN1C(=O)C2=C(NCCN(C(=O)Cc3ccccc3)C2c2ccc(F)cc2)C1(C)C] | NUCC-0202493 | |
| 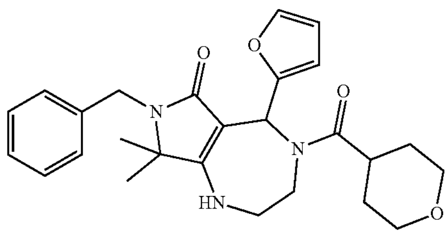 [SMILES: CC1(C)C2=C(C(=O)N1Cc1ccccc1)C(c1ccco1)N(C(=O)C1CCOCC1)CCN2] | NUCC-0077068 | |
| 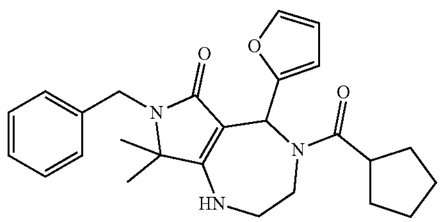 [SMILES: CC1(C)C2=C(C(=O)N1Cc1ccccc1)C(c1ccco1)N(C(=O)C1CCCC1)CCN2] | NUCC-0077067 | 8s |
| 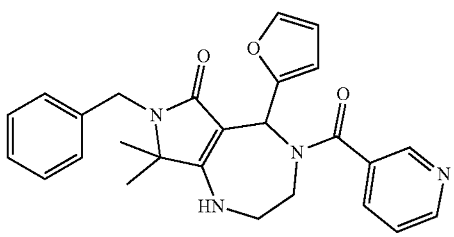 [SMILES: CC1(C)C2=C(C(=O)N1Cc1ccccc1)C(c1ccco1)N(C(=O)c1cccnc1)CCN2] | NUCC-0077066 | 8r |
| 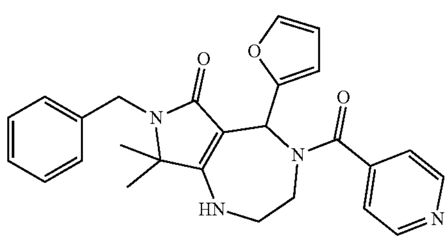 [SMILES: CC1(C)C2=C(C(=O)N1Cc1ccccc1)C(c1ccco1)N(C(=O)c1ccncc1)CCN2] | NUCC-0077065 | 8q |
| 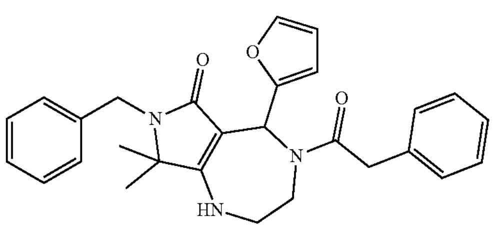 [SMILES: CC1(C)C2=C(C(=O)N1Cc1ccccc1)C(c1ccco1)N(C(=O)Cc1ccccc1)CCN2] | NUCC-0077064 | 8p |

TABLE 2-continued

Synthesized Molecules and Compounds

| Structure | Molecule Name | Compound ID |
| --- | --- | --- |
| 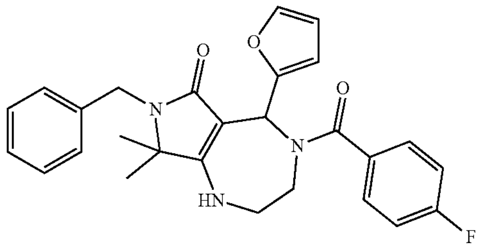 [SMILES: CC1(C)C2=C(C(=O)N1Cc1ccccc1)C(c1ccco1)N(C(=O)c1ccc(F)cc1)CCN2] | NUCC-0077063 | 8o |
| 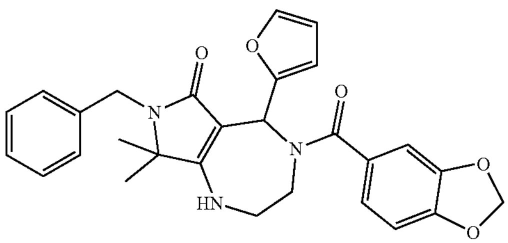 [SMILES: CC1(C)C2=C(C(=O)N1Cc1ccccc1)C(c1ccco1)N(C(=O)c1ccc3c(c1)OCO3)CCN2] | NUCC-0077062 | 8n |
| 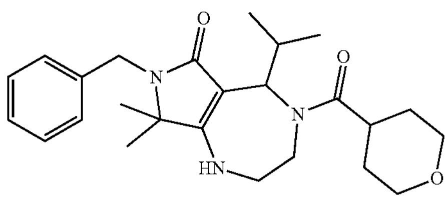 [SMILES: CC(C)C1C2=C(NCCN1C(=O)C1CCOCC1)C(C)(C)N(Cc1ccccc1)C2=O] | NUCC-0077061 | 8d |
| 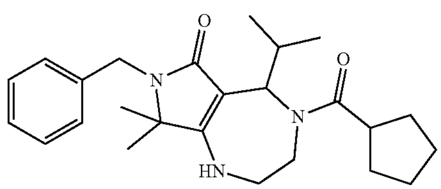 [SMILES: CC(C)C1C2=C(NCCN1C(=O)C1CCCC1)C(C)(C)N(Cc1ccccc1)C2=O] | NUCC-0077060 | 8c |
| 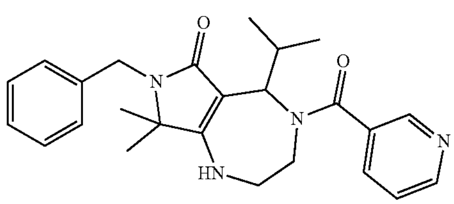 [SMILES: CC(C)C1C2=C(NCCN1C(=O)c1cccnc1)C(C)(C)N(Cc1ccccc1)C2=O] | NUCC-0077059 | 8f |
| 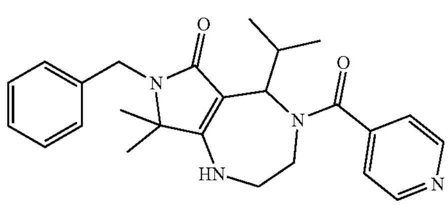 [SMILES: CC(C)C1C2=C(NCCN1C(=O)c1ccncc1)C(C)(C)N(Cc1ccccc1)C2=O] | NUCC-0077058 | 8e |
| 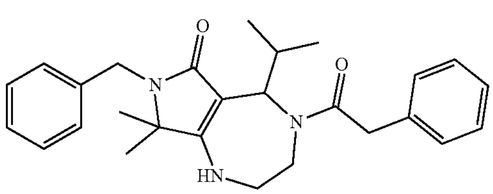 [SMILES: CC(C)C1C2=C(NCCN1C(=O)Cc1ccccc1)C(C)(C)N(Cc1ccccc1)C2=O] | NUCC-0077057 | 8i |

TABLE 2-continued

Synthesized Molecules and Compounds

| Structure | Molecule Name | Compound ID |
|---|---|---|
| 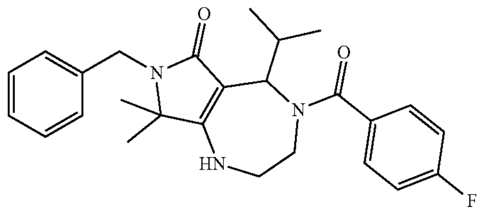 [SMILES: CC(C)C1C2=C(NCCN1C(=O)c1ccc(F)cc1)C(C)(C)N(Cc1ccccc1)C2=O] | NUCC-0077056 | 8h |
| 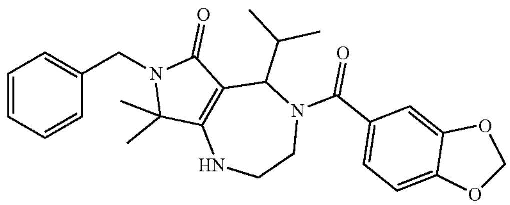 [SMILES: CC(C)C1C2=C(NCCN1C(=O)c1ccc3c(c1)OCO3)C(C)(C)N(Cc1ccccc1)C2=O] | NUCC-0077055 | 8g |
| 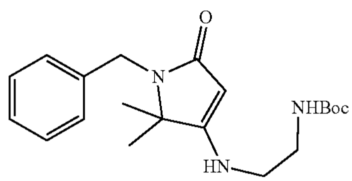 [SMILES: CC(C)(C)OC(=O)NCCNC1=CC(=O)N(Cc2ccccc2)C1(C)C] | NUCC-0077054 | |
| 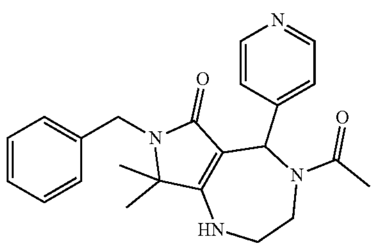 [SMILES: CC(=O)N1CCNC2=C(C(=O)N(Cc3ccccc3)C2(C)C)C1c1ccncc1] | NUCC-0077053 | |
| 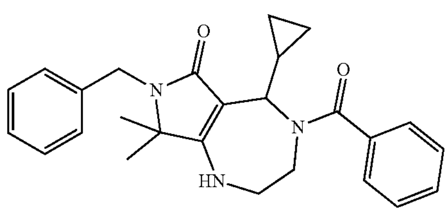 [SMILES: CC1(C)C2=C(C(=O)N1Cc1ccccc1)C(C1CC1)N(C(=O)c1ccccc1)CCN2] | NUCC-0077052 | 8y |
| 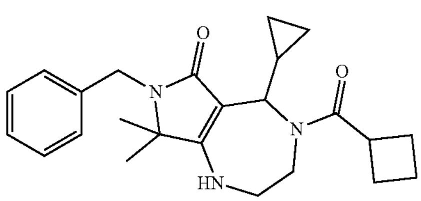 [SMILES: CC1(C)C2=C(C(=O)N1Cc1ccccc1)C(C1CC1)N(C(=O)C1CCC1)CCN2] | NUCC-0077051 | 8x |
| 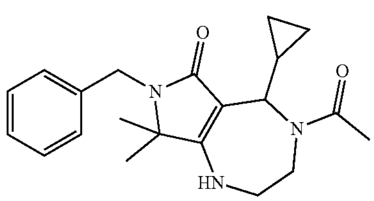 [SMILES: CC(=O)N1CCNC2=C(C(=O)N(Cc3ccccc3)C2(C)C)C1C1CC1] | NUCC-0077050 | 8w |

TABLE 2-continued

Synthesized Molecules and Compounds

| Structure | Molecule Name | Compound ID |
|---|---|---|
| 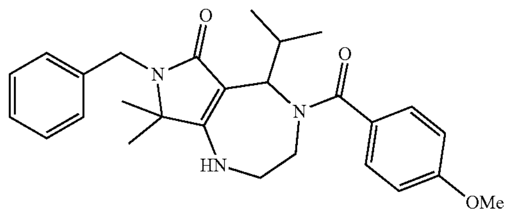 [SMILES: COc1ccc(C(=O)N2CCNC3=C(C(=O)N(Cc4ccccc4)C3(C)C)C2C(C)C)cc1] | NUCC-0077049 | 8l |
| 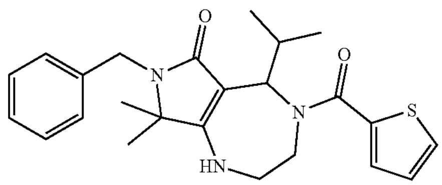 [SMILES: CC(C)C1C2=C(NCCN1C(=O)c1cccs1)C(C)(C)N(Cc1ccccc1)C2=O] | NUCC-0077048 | 8k |
| 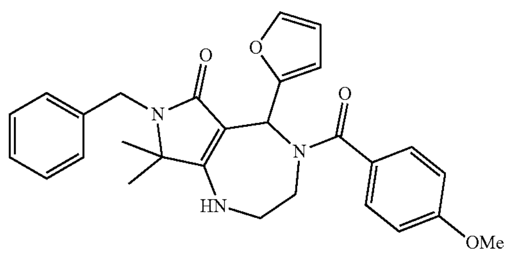 [SMILES: COc1ccc(C(=O)N2CCNC3=C(C(=O)N(Cc4ccccc4)C3(C)C)C2c2ccco2)cc1] | NUCC-0077047 | 8v |
| 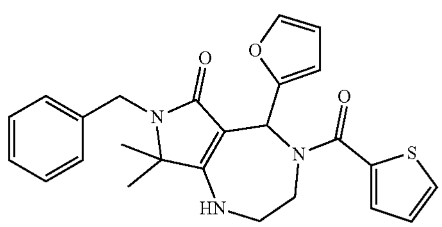 [SMILES: CC1(C)C2=C(C(=O)N1Cc1ccccc1)C(c1ccco1)N(C(=O)c1cccs1)CCN2] | NUCC-0077046 | 8u |
| 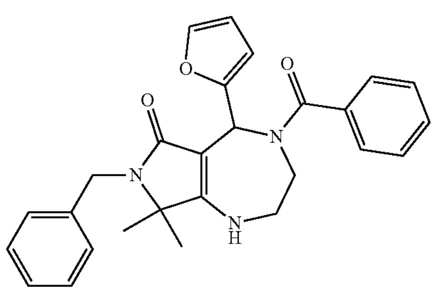 [SMILES: CC1(C)C2=C(C(=O)N1Cc1ccccc1)C(c1ccco1)N(C(=O)c1ccccc1)CCN2] | NUCC-0077045 | 8t |
| 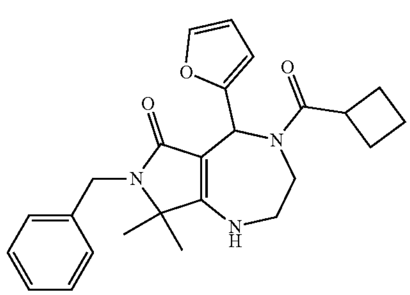 [SMILES: CC1(C)C2=C(C(=O)N1Cc1ccccc1)C(c1ccco1)N(C(=O)C1CCC1)CCN2] | NUCC-0077044 | 8m |

TABLE 2-continued

Synthesized Molecules and Compounds

| Structure | Molecule Name | Compound ID |
|---|---|---|
| 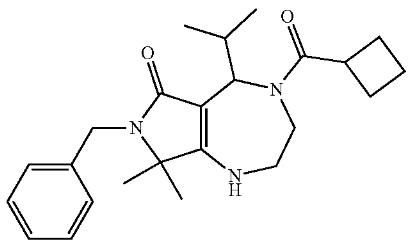 [SMILES: CC(C)C1C2=C(NCCN1C(=O)C1CCC1)C(C)(C)N(Cc1ccccc1)C2=O] | NUCC-0077043 | 8b |
| 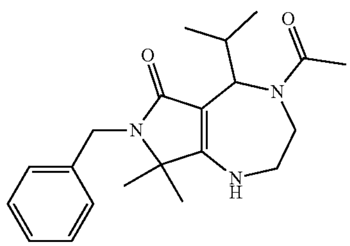 [SMILES: CC(=O)N1CCNC2=C(C(=O)N(Cc3ccccc3)C2(C)C)C1C(C)C] | NUCC-0077042 | 8a |
| 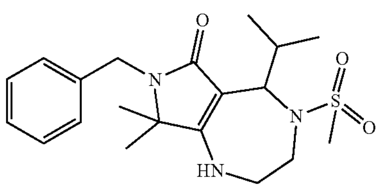 [SMILES: CC(C)C1C2=C(NCCN1S(C)(=O)=O)C(C)(C)N(Cc1ccccc1)C2=O] | NUCC-0075249 | 8j |
| 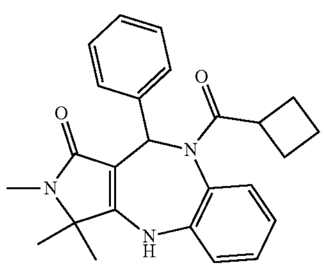 [SMILES: CN1C(=O)C2=C(Nc3ccccc3N(C(=O)C3CCC3)C2c2ccccc2)C1(C)C] | NUCC-0060873 | |
| 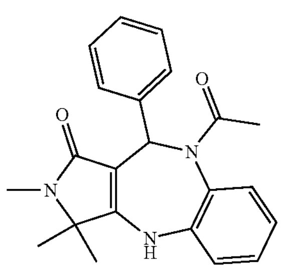 [SMILES: CC(=O)N1c2ccccc2NC2=C(C(=O)N(C)C2(C)C)C1c1ccccc1] | NUCC-0060872 | |
| 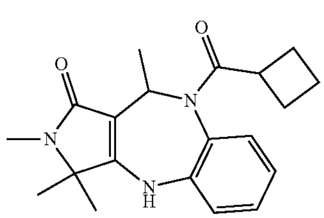 [SMILES: CC1C2=C(Nc3ccccc3N1C(=O)C1CCC1)C(C)(C)N(C)C2=O] | NUCC-0060871 | |

TABLE 2-continued

Synthesized Molecules and Compounds

| Structure | Molecule Name Compound ID |
|---|---|
| 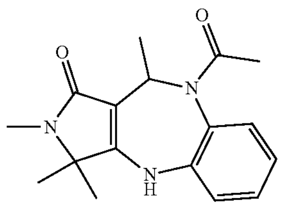 [SMILES: CC(=O)N1c2ccccc2NC2=C(C(=O)N(C)C2(C)C)C1C] | NUCC-0060870 |
| 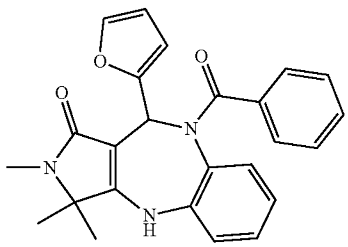 [SMILES: CN1C(=O)C2=C(Nc3ccccc3N(C(=O)c3ccccc3)C2c2ccco2)C1(C)C] | NUCC-0060869 |
| 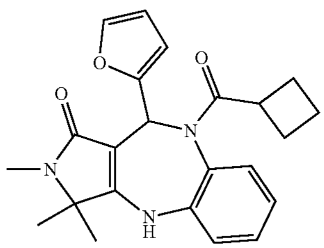 [SMILES: CN1C(=O)C2=C(Nc3ccccc3N(C(=O)C3CCC3)C2c2ccco2)C1(C)C] | NUCC-0060868 |
| 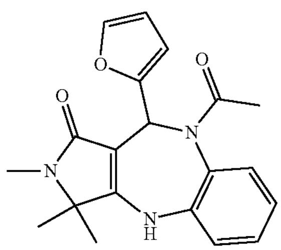 [SMILES: CC(=O)N1c2ccccc2NC2=C(C(=O)N(C)C2(C)C)C1c1ccco1] | NUCC-0060867 |
| 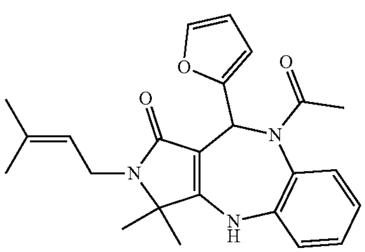 [SMILES: CC(=O)N1c2ccccc2NC2=C(C(=O)N(CC=C(C)C)C2(C)C)C1c1ccco1] | NUCC-0060866 |
| 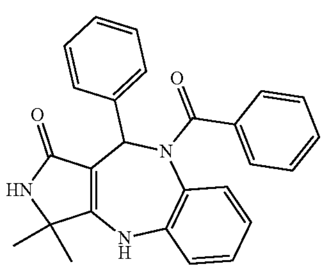 [SMILES: CC1(C)NC(=O)C2=C1Nc1ccccc1N(C(=O)c1ccccc1)C2c1ccccc1] | NUCC-0060865 |

TABLE 2-continued
Synthesized Molecules and Compounds
| Structure | Molecule Name | Compound ID |
|---|---|---|
| 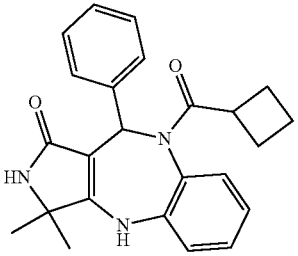 [SMILES: CC1(C)NC(=O)C2=C1Nc1ccccc1N(C(=O)C1CCC1)C2c1ccccc1] | | NUCC-0060864 |
| 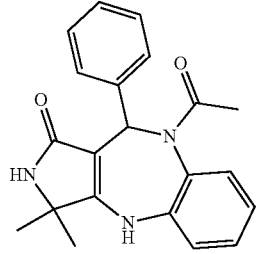 [SMILES: CC(=O)N1c2ccccc2NC2=C(C(=O)NC2(C)C)C1c1ccccc1] | | NUCC-0060863 |
| 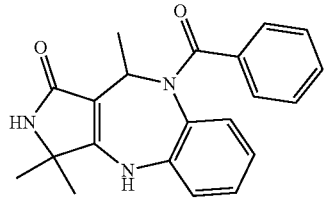 [SMILES: CC1C2=C(Nc3ccccc3N1C(=O)c1ccccc1)C(C)(C)NC2=O] | | NUCC-0060862 |
| 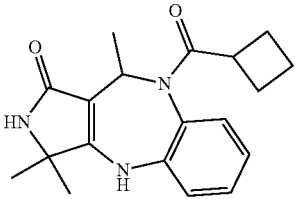 [SMILES: CC1C2=C(Nc3ccccc3N1C(=O)C1CCC1)C(C)(C)NC2=O] | | NUCC-0060861 |
| 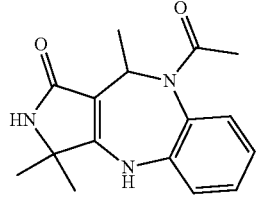 [SMILES: CC(=O)N1c2ccccc2NC2=C(C(=O)NC2(C)C)C1C] | | NUCC-0060860 |
| 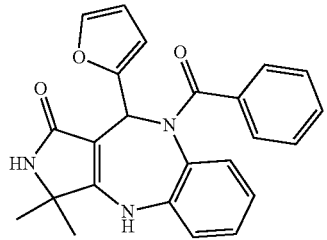 [SMILES: CC1(C)NC(=O)C2=C1Nc1ccccc1N(C(=O)c1ccccc1)C2c1ccco1] | | NUCC-0060859 |

TABLE 2-continued

Synthesized Molecules and Compounds

| Structure | Molecule Name | Compound ID |
|---|---|---|
| | | NUCC-0060858 |
| | | NUCC-0060857 |
| | | NUCC-0060856 |
| | | NUCC-0060855 |
| | | NUCC-0060854 |
| | | NUCC-0054368 |

TABLE 2-continued

Synthesized Molecules and Compounds

| Structure | Molecule Name | Compound ID |
|---|---|---|
| | | NUCC-0054140 |

Assay Protocol for Anti-Cancer Activity

Anti-cancer activity screening of all compounds was performed by the NCI Developmental Therapeutics Program (DTP) through their NCI60 screening initiative. Assay details can be found at the website dtp.cancer.gov/discovery_development/nci-60/methodology.htm. Information from this website is reproduced here for convenience.

NCI-60 Screening Methodology/NCI 60 Cell One-Dose Screen

General Description

As of early 2007 all compounds submitted to the NCI 60 Cell screen are tested initially at a single high dose (10-5 M) in the full NCI 60 cell panel. Only compounds which satisfy pre-determined threshold inhibition criteria in a minimum number of cell lines will progress to the full 5-dose assay. The threshold inhibition criteria for progression to the 5-dose screen was selected to efficiently capture compounds with anti-proliferative activity based on careful analysis of historical DTP screening data. The threshold criteria may be updated as additional data becomes available.

Interpretation of One-Dose Data

The One-dose data will be reported as a mean graph of the percent growth of treated cells and will be similar in appearance to mean graphs from the 5-dose assay. The number reported for the One-dose assay is growth relative to the no-drug control, and relative to the time zero number of cells. This allows detection of both growth inhibition (values between 0 and 100) and lethality (values less than 0). This is the same as for the 5-dose assay, described below. For example, a value of 100 means no growth inhibition. A value of 40 would mean 60% growth inhibition. A value of 0 means no net growth over the course of the experiment. A value of −40 would mean 40% lethality. A value of −100 means all cells are dead. Information from the One-dose mean graph is available for COMPARE analysis.

NCI 60 Cell Five-Dose Screen

Compounds which exhibit significant growth inhibition in the One-Dose Screen are evaluated against the 60 cell panel at five concentration levels.

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters are calculated for each experimental agent. Growth inhibition of 50% (GI50) is calculated from $[(Ti-Tz)/(C-Tz)] \times 100 = 50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from

[(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested.

TABLE 3

Growth Inhibition of NUCC-608455 on NCI60 Cell Line Panel

| Panel/Cell Line | Growth Percent |
| --- | --- |
| Leukemia | |
| CCRF-CEM | 24.15 |
| HL-60(TB) | 9.63 |
| K-562 | 12.60 |
| MOLT-4 | 28.58 |
| RPMI-8226 | 23.43 |
| SR | 23.29 |
| Non-Small Cell Lung Cancer | |
| A549/ATCC | 22.02 |
| EKVX | 35.37 |
| HOP-62 | 33.09 |
| HOP-92 | 21.07 |
| NCI-H226 | 65.66 |
| NCI-H23 | 20.85 |
| NCI-H322M | 44.61 |
| NCI-H460 | 4.83 |
| NCI-H522 | 21.79 |
| Colon Cancer | |
| COLO 205 | 16.77 |
| HCC-2998 | 3.73 |
| HCT-116 | 7.52 |
| HCT-15 | 15.65 |
| HT29 | 9.99 |
| KM12 | 14.83 |
| SW-620 | 21.68 |
| CNS Cancer | |
| SF-268 | 42.68 |
| SF-295 | −0.75 |
| SF-539 | −17.85 |
| SNB-19 | 23.61 |
| SNB-75 | 16.83 |
| U251 | 24.64 |
| Melanoma | |
| LOX IMVI | 25.57 |
| MALME-3M | 69.89 |
| M14 | −13.58 |
| MDA-MB-435 | −56.24 |
| SK-MEL-2 | 16.91 |
| SK-MEL-28 | 57.26 |
| SK-MEL-5 | 7.88 |
| UACC-257 | 77.61 |
| UACC-62 | 21.25 |
| Ovarian Cancer | |
| IGROV1 | 26.78 |
| OVCAR-3 | −7.65 |
| OVCAR-4 | 48.83 |
| OVCAR-5 | 25.92 |
| OVCAR-8 | 26.13 |
| NCI/ADR-RES | 82.92 |
| SK-OV-3 | 22.71 |
| Renal Cancer | |
| 786-0 | 21.45 |
| ACHN | 33.51 |
| CAKI-1 | 42.97 |
| RXF 393 | −11.72 |
| SN12C | 35.91 |
| TK-10 | 54.92 |
| UO-31 | 52.54 |
| Prostate Cancer | |
| PC-3 | 29.67 |
| DU-145 | 7.82 |
| Breast Cancer | |
| MCF7 | 15.26 |
| MDA-MB-231/ATCC | 9.25 |
| HS 578T | 10.67 |
| BT-549 | 47.62 |
| T-47D | 35.10 |
| MDA-MB-468 | −1.86 |
| Mean | 23.48 |
| Delta | 79.72 |
| Range | 139.16 |

TABLE 4

Growth Inhibition of NUCC-60872 on NCI60 Cell Line Panel

| Panel/Cell Line | Growth Percent |
| --- | --- |
| Leukemia | |
| CCRF-CEM | 20.66 |
| HL-60(TB) | 7.50 |
| K-562 | 16.57 |
| MOLT-4 | 33.27 |
| RPMI-8226 | 12.61 |
| SR | 16.70 |
| Non-Small Cell Lung Cancer | |
| A549/ATCC | 80.32 |
| EKVX | 61.53 |
| HOP-62 | 61.59 |
| HOP-92 | 37.54 |
| NCI-H226 | 91.06 |
| NCI-H23 | 50.21 |
| NCI-H322M | 73.36 |
| NCI-H460 | 21.87 |
| NCI-H522 | 18.58 |
| Colon Cancer | |
| COLO 205 | 14.23 |
| HCC-2998 | 60.81 |
| HCT-116 | 24.91 |
| HCT-15 | 93.83 |
| HT29 | 25.22 |
| KM12 | 19.79 |
| SW-620 | 24.24 |
| CNS Cancer | |
| SF-268 | 42.99 |
| SF-295 | 45.97 |
| SF-539 | 20.14 |
| SNB-19 | 39.87 |
| SNB-75 | −3.29 |
| U251 | 18.07 |
| Melanoma | |
| LOX IMVI | 37.52 |
| MALME-3M | 44.26 |
| M14 | 21.48 |
| MDA-MB-435 | −67.83 |
| SK-MEL-2 | 8.92 |
| SK-MEL-28 | 56.02 |
| SK-MEL-5 | 27.50 |
| UACC-257 | 36.37 |
| UACC-62 | 32.33 |

TABLE 4-continued

Growth Inhibition of NUCC-60872 on NCI60 Cell Line Panel

| Panel/Cell Line | Growth Percent |
|---|---|
| Ovarian Cancer | |
| IGROV1 | 39.64 |
| OVCAR-3 | 18.09 |
| OVCAR-4 | 55.16 |
| OVCAR-5 | 62.50 |
| OVCAR-8 | 65.84 |
| NCI/ADR-RES | 101.74 |
| SK-OV-3 | 55.42 |
| Renal Cancer | |
| 786-0 | 80.09 |
| ACHN | 95.96 |
| CAKI-1 | 71.91 |
| RXF 393 | 27.79 |
| SN12C | 40.74 |
| TK-10 | 87.08 |
| UO-31 | 81.99 |
| Prostate Cancer | |
| PC-3 | 36.41 |
| DU-145 | 78.98 |
| Breast Cancer | |
| MCF7 | 16.41 |
| MDA-MB-231/ATCC | 63.32 |
| HS 57BT | 20.42 |
| BT-549 | 69.46 |
| T-47D | 28.72 |
| MDA-MB-468 | 19.19 |
| Mean | 41.43 |
| Delta | 109.26 |
| Range | 169.57 |

REFERENCES

1. Lovering, F.; Bikker, J.; Humblet, C., Escape from flatland: increasing saturation as an approach to improving clinical success. J Med Chem 2009, 52 (21), 6752-6.
2. Horton, D. A.; Bourne, G. T.; Smythe, M. L., The combinatorial synthesis of bicyclic privileged structures or privileged substructures. Chemical reviews 2003, 103 (3), 893-930.
3. Welsch, M. E.; Snyder, S. A.; Stockwell, B. R., Privileged scaffolds for library design and drug discovery. Curr Opin Chem Biol 2010, 14 (3), 347-61.
4. Di Braccio, M.; Grossi, G.; Roma, G.; Vargiu, L.; Mura, M.; Marongiu, M. E., 1,5-Benzodiazepines. Part XII. Synthesis and biological evaluation of tricyclic and tetracyclic 1,5-benzodiazepine derivatives as nevirapine analogues. European journal of medicinal chemistry 2001, 36 (11-12), 935-49.
5. Merluzzi, V. J.; Hargrave, K. D.; Labadia, M.; Grozinger, K.; Skoog, M.; Wu, J. C.; Shih, C. K.; Eckner, K.; Hattox, S.; Adams, J.; et al., Inhibition of HIV-1 replication by a nonnucleoside reverse transcriptase inhibitor. Science 1990, 250 (4986), 1411-3.
6. Filippakopoulos, P.; Qi, J.; Picaud, S.; Shen, Y.; Smith, W. B.; Fedorov, O.; Morse, E. M.; Keates, T.; Hickman, T. T.; Felletar, I.; Philpott, M.; Munro, S.; McKeown, M. R.; Wang, Y.; Christie, A. L.; West, N.; Cameron, M. J.; Schwartz, B.; Heightman, T. D.; La Thangue, N.; French, C. A.; Wiest, O.; Kung, A. L.; Knapp, S.; Bradner, J. E., Selective inhibition of BET bromodomains. Nature 2010, 468 (7327), 1067-73.
7. Nicodeme, E.; Jeffrey, K. L.; Schaefer, U.; Beinke, S.; Dewell, S.; Chung, C. W.; Chandwani, R.; Marazzi, I.; Wilson, P.; Coste, H.; White, J.; Kirilovsky, J.; Rice, C. M.; Lora, J. M.; Prinjha, R. K.; Lee, K.; Tarakhovsky, A., Suppression of inflammation by a synthetic histone mimic Nature 2010, 468 (7327), 1119-23.
8. Rosenstrom, U.; Skold, C.; Lindeberg, G.; Botros, M.; Nyberg, F.; Karlen, A.; Hallberg, A., Design, synthesis, and incorporation of a beta-turn mimetic in angiotensin II forming novel pseudopeptides with affinity for AT1 and AT2 receptors. J Med Chem 2006, 49 (20), 6133-7.
9. Jeong, Y.-C.; Moloney, M. G., Tetramic Acids as Scaffolds: Synthesis, Tautomeric and Antibacterial Behaviour. Synlett 2009, 2009 (15), 2487-2491.
10. Holloway, C. A.; Matthews, C. J.; Jeong, Y. C.; Moloney, M. G.; Roberts, C. F.; Yaqoob, M., Novel chiral skeletons for drug discovery: antibacterial tetramic acids. Chemical biology & drug design 2011, 78 (2), 229-35.
11. Royles, B. J. L., Naturally Occurring Tetramic Acids: Structure, Isolation, and Synthesis. Chemical reviews 1995, 95 (6), 1981-2001.
12. Cui, J.; Matsumoto, K.; Wang, C. Y.; Peter, M. E.; Kozmin, S. A., Synthesis of a high-purity chemical library reveals a potent inducer of oxidative stress. Chembiochem: a European journal of chemical biology 2010, 11 (9), 1224-7.
13. Matsuo, K.; Tanaka, K., Syntheses of the Novel Furo [3, 4-b] [1, 5] benzodiazepinone and Pyrrolo [3, 4-b] [1, 5] benzodiazepinone Systems. Chem Pharm Bull 1984, 32 (9), 3724-3729.
14. Lipinski, C. A.; Lombardo, F.; Dominy, B. W.; Feeney, P. J., Experimental and computational approaches to estimate solubility and permeability in drug discovery and development settings. Adv. Drug Deliv. Rev. 1997, 23 (1-3), 3-25.
15. Shoemaker, R. H., The NCI60 human tumour cell line anticancer drug screen. Nat. Rev. Cancer 2006, 6 (10), 813-23.
16. Boyd, M. R.; Paull, K. D., Some practical considerations and applications of the national cancer institute in vitro anticancer drug discovery screen. Drug Development Research 1995, 34 (2), 91-109.
17. Skehan, P.; Storeng, R.; Scudiero, D.; Monks, A.; McMahon, J.; Vistica, D.; Warren, J. T.; Bokesch, H.; Kenney, S.; Boyd, M. R., New colorimetric cytotoxicity assay for anticancer-drug screening. J Natl Cancer Inst 1990, 82 (13), 1107-12.
18. Arkin, M. R.; Wells, J. A., Small-molecule inhibitors of protein-protein interactions: progressing towards the dream. Nat Rev Drug Discov 2004, 3 (4), 301-17.
19. Souers, A. J.; Leverson, J. D.; Boghaert, E. R.; Ackler, S. L.; Catron, N. D.; Chen, J.; Dayton, B. D.; Ding, H.; Enschede, S. H.; Fairbrother, W. J.; Huang, D. C.; Hymowitz, S. G.; Jin, S.; Khaw, S. L.; Kovar, P. J.; Lam, L. T.; Lee, J.; Maecker, H. L.; Marsh, K. C.; Mason, K. D.; Mitten, M. J.; Nimmer, P. M.; Oleksijew, A.; Park, C. H.; Park, C. M.; Phillips, D. C.; Roberts, A. W.; Sampath, D.; Seymour, J. F.; Smith, M. L.; Sullivan, G. M.; Tahir, S. K.; Tse, C.; Wendt, M. D.; Xiao, Y.; Xue, J. C.; Zhang, H.; Humerickhouse, R. A.; Rosenberg, S. H.; Elmore, S. W., ABT-199, a potent and selective BCL-2 inhibitor, achieves antitumor activity while sparing platelets. Nature medicine 2013, 19 (2), 202-8.
20. Rzuczek, S. G.; Colgan, L. A.; Nakai, Y.; Cameron, M. D.; Furling, D.; Yasuda, R.; Disney, M. D., Precise small-molecule recognition of a toxic CUG RNA repeat expansion. Nat Chem Biol 2017, 13 (2), 188-193.

21. Velagapudi, S. P.; Cameron, M. D.; Haga, C. L.; Rosenberg, L. H.; Lafitte, M.; Duckett, D. R.; Phinney, D. G.; Disney, M. D., Design of a small molecule against an oncogenic noncoding RNA. Proc Natl Acad Sci USA 2016, 113 (21), 5898-903.
22. Lipinski, C.; Hopkins, A., Navigating chemical space for biology and medicine. Nature 2004, 432 (7019), 855-61.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound or a salt thereof having a formula:

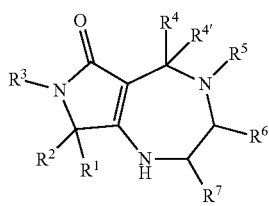

wherein:
$R^1$ and $R^2$ are methyl;
$R^3$ is H or methyl, or benzyl;
$R^4$ is $C_1$-$C_3$ alkyl, benzyl, a carbocycle, a heterocycle, or a fused carbocycle and heterocycle, which carbocycle and heterocycle are saturated or unsaturated at one or more bonds, and $R^4$ optionally is substituted at one or more positions with halo or carboxyl;
$R^{4'}$ is H;
$R^5$ has a formula

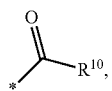

wherein $R^{10}$ is methyl, phenylamino, amino, or benzyl, or $R^{10}$ is a carbocycle, a heterocycle, which carbocycle and heterocycle are saturated or unsaturated at one or more bonds; or $R^{10}$ has a formula

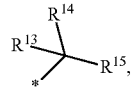

wherein $R^{13}$ is H, $R^{14}$ is H, $R^{15}$ is a heterocycle; and
$R^6$ and $R^7$ together form phenyl fused to the 1.4-diazepine core;
with the proviso that if $R^3$ is hydrogen, then (i) $R^{10}$ is a carbocycle, which carbocycle is saturated or unsaturated at one or more bonds, or (ii) $R^4$ is a heterocycle, which heterocycle is saturated or unsaturated at one or more bonds; and
with the proviso that if $R^3$ is benzyl, then (i) $R^{10}$ is methyl and $R^4$ is $C_1$-$C_3$ alkyl or furanyl, or (ii) $R^{10}$ is $C_4$-$C_8$ cycloalkyl and $R^4$ is $C_1$-$C_3$ alkyl.
2. The compound of claim 1, wherein $R^3$ is methyl.
3. The compound of claim 1, wherein $R^4$ is selected from methyl, isopropyl, furanyl, pyridinyl, phenyl, fluorophenyl, carboxyphenyl, benzyl, 1,3-benzodioxolyl, and piperidinyl.
4. The compound of claim 1, wherein $R^{10}$ is methyl, cyclopropyl, cyclobutyl, phenyl, thiophenyl, 4-(N,N-diakylamino)phenyl, pyridinyl, dialkylamino, piperidinyl, or benzyl.
5. The compound of claim 1, wherein $R^5$ has a formula

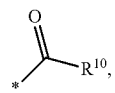

$R^{10}$ has a formula

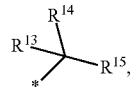

$R^{13}$ is H, $R^{14}$ is H, and $R^{15}$ is tetrahydropyranyl.
6. The compound of claim 1, wherein $R^4$ is benzyl or phenyl.
7. The compound of claim 1, wherein $R^5$ is acetyl.
8. A pharmaceutical composition comprising any effective amount of the compound of claim 1 and a pharmaceutical carrier, excipient, or diluent.
9. A method for treating cancer in a subject in need thereof, the method comprising administering to the subject the pharmaceutical composition of claim 8.
10. A compound having a formula selected from:

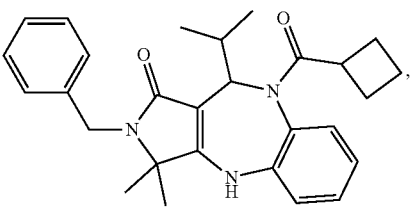

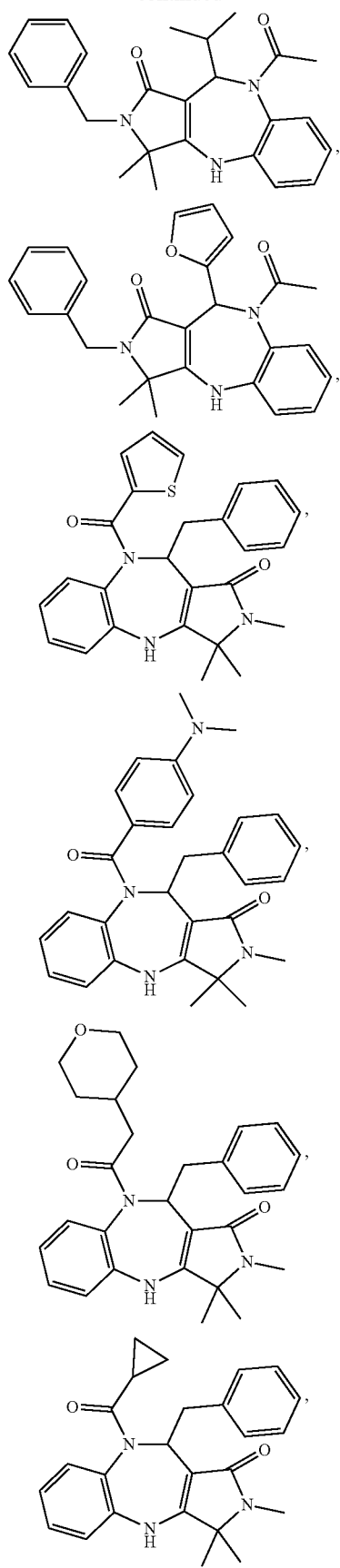
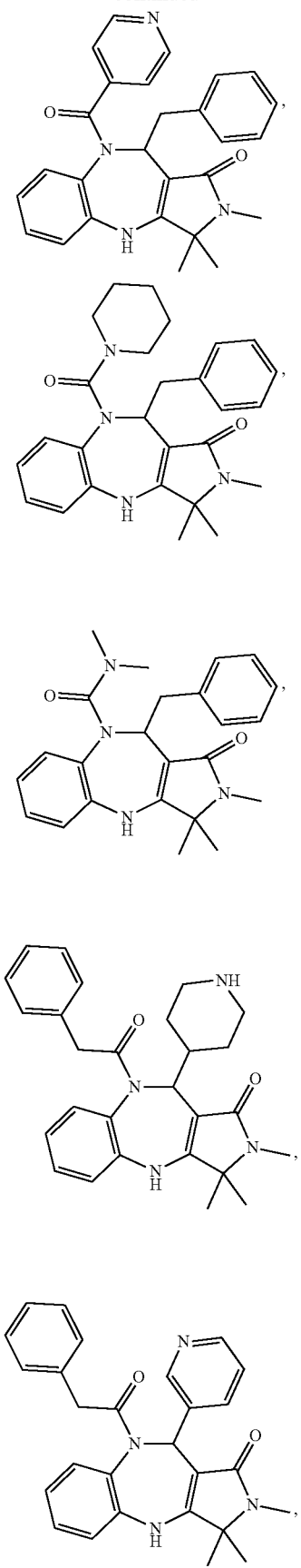

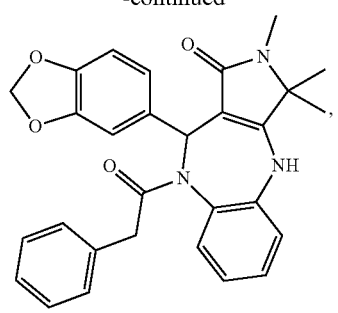
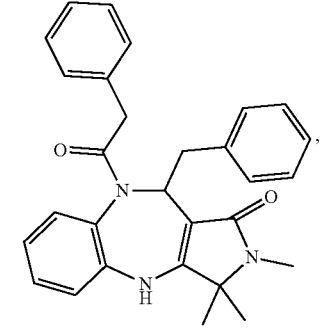
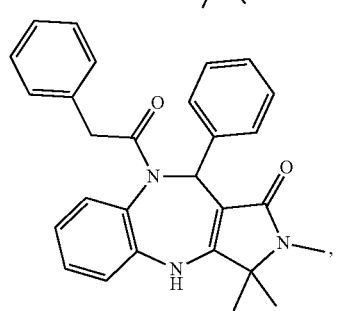
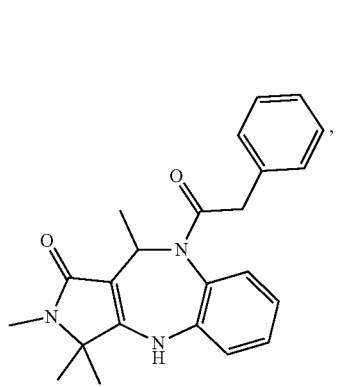
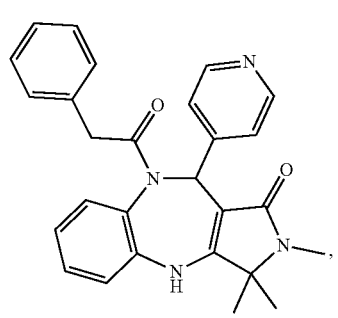
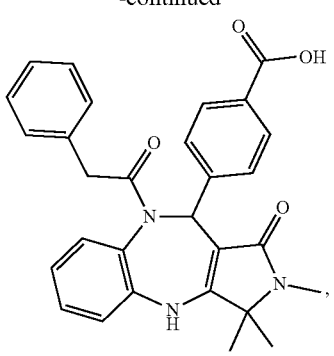
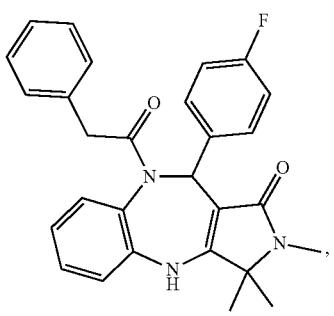
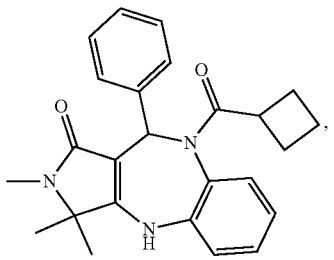
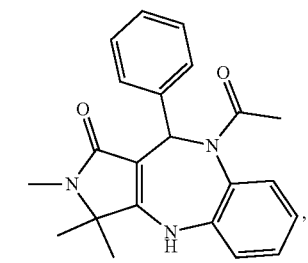
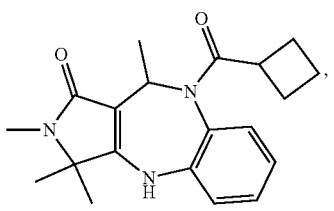
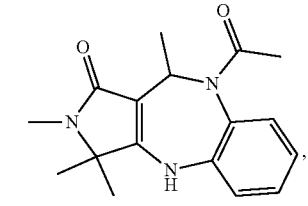

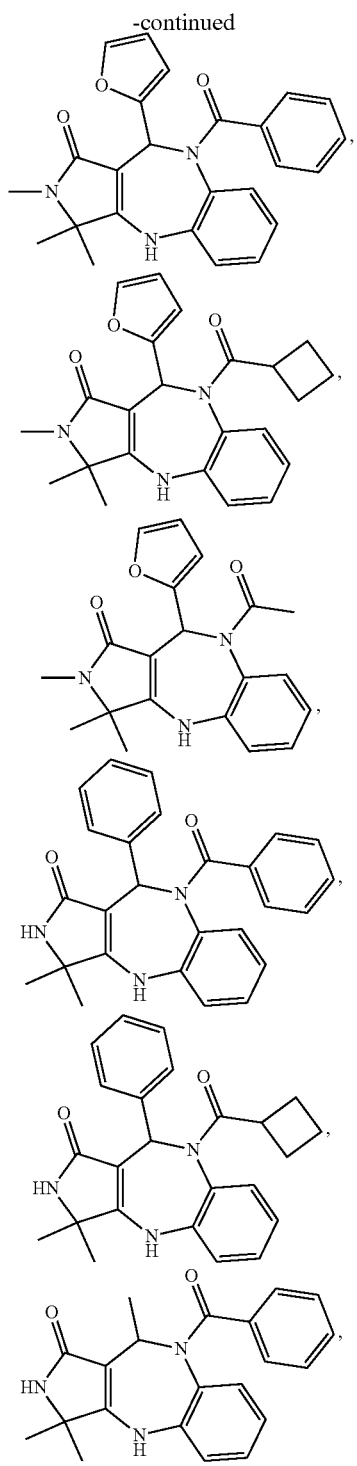
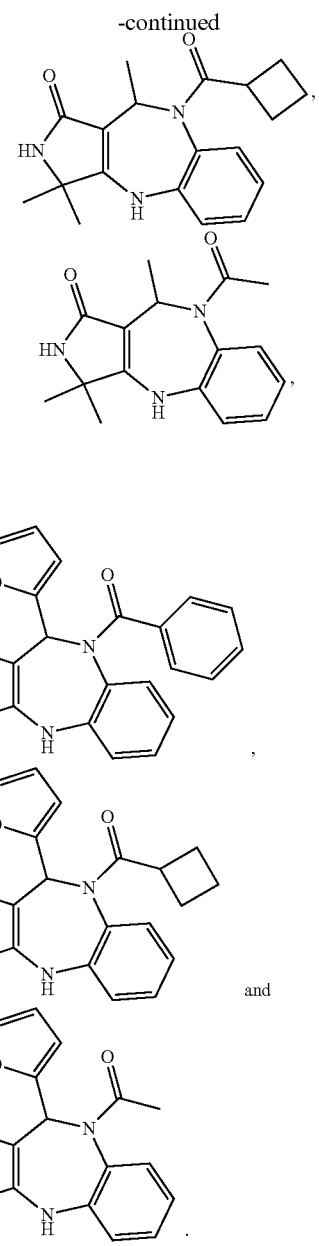
11. A pharmaceutical composition comprising any effective amount of the compound of claim 10 and a pharmaceutical carrier, excipient, or diluent.
12. A method for treating cancer in a subject in need thereof, the method comprising administering to the subject the pharmaceutical composition of claim 11.
* * * * *